(12) United States Patent
Suchomel et al.

(10) Patent No.: US 11,759,280 B2
(45) Date of Patent: Sep. 19, 2023

(54) SURGICAL INSTRUMENTATION FOR FIXATION OF CERVICAL SPINE

(71) Applicants: Aesculap Implant Systems, LLC, Center Valley, PA (US); Aesculap AG, Tuttlingen (DE)

(72) Inventors: Petr Suchomel, Liberec (CZ); Ralph Kothe, Hamberg (DE); Tamara Leder, Tuttlingen (DE); Ernie Corrao, Bethel, CT (US); Scott Larsen, Newtown, CT (US); Kehui Chen, Seymour, CT (US); Christopher Schwartz, Middlebury, CT (US); Nicole Sroka, Seymour, CT (US); Ron Litke, Sandy Hook, CT (US)

(73) Assignee: Aesculap AG, Tuttlingen (DE)

( * ) Notice: Subject to any disclaimer, the term of this patent is extended or adjusted under 35 U.S.C. 154(b) by 68 days.

(21) Appl. No.: 17/164,145

(22) Filed: Feb. 1, 2021

(65) Prior Publication Data
US 2021/0244424 A1 Aug. 12, 2021

Related U.S. Application Data

(60) Provisional application No. 62/970,850, filed on Feb. 6, 2020.

(51) Int. Cl.
*A61B 17/16* (2006.01)
*A61B 17/17* (2006.01)
*A61B 90/00* (2016.01)

(52) U.S. Cl.
CPC .......... *A61B 90/03* (2016.02); *A61B 17/1617* (2013.01); *A61B 17/1633* (2013.01); *A61B 17/1637* (2013.01); *A61B 17/1671* (2013.01); *A61B 17/1697* (2013.01); *A61B 17/1757* (2013.01); *A61B 17/1796* (2013.01); *A61B 90/06* (2016.02); *A61B 2090/034* (2016.02); *A61B 2090/062* (2016.02)

(58) Field of Classification Search
CPC ........................... A61B 17/1697; A61B 90/03
See application file for complete search history.

(56) References Cited

U.S. PATENT DOCUMENTS

| | | | |
|---|---|---|---|
| 6,716,215 B1 * | 4/2004 | David | A61B 17/1622 433/116 |
| 2004/0146367 A1 * | 7/2004 | Gerhardt | B25F 5/003 408/110 |

(Continued)

*Primary Examiner* — Christian A Sevilla

(57) ABSTRACT

A universal drill guide system includes a universal drill guide, interchangeable drill tubes, and interchangeable drill bits. Each interchangeable drill tube corresponds to one of the interchangeable drill bits, and can be detachably coupled to the universal drill guide. A cannulated drill with K-wire retention features a drill bit with a retention mechanism that prevents axial advancement of a K-wire during drilling. A drill removal tool includes a drill remover that can be placed around a drill bit to remove it from bone after a hole is drilled, while leaving a K-wire in place in the bone. A bone screw driver with K-wire retention includes a shaft that can be passed over a K-wire, a distal end for attachment to a cannulated bone screw, and a K-wire retention module for preventing advancement of the K-wire as the screw driver drives the cannulated bone screw into bone.

7 Claims, 23 Drawing Sheets

(56) References Cited

U.S. PATENT DOCUMENTS

2006/0189997 A1* 8/2006 Guenther ............. A61B 17/808
                                                    606/88
2014/0228848 A1* 8/2014 Torrie ................ A61B 17/1746
                                                    606/80
2016/0367294 A1* 12/2016 Boyd .................... A61F 2/4601

* cited by examiner

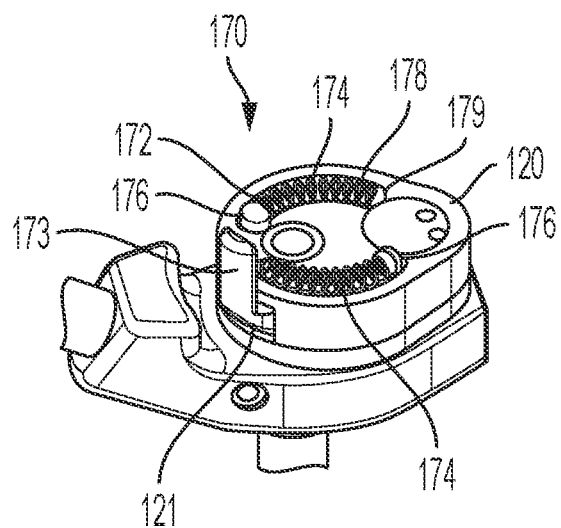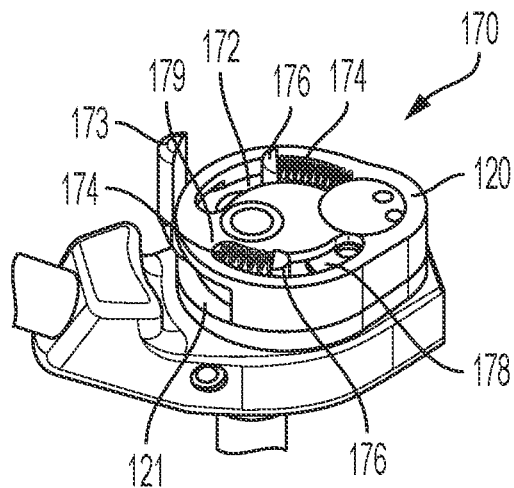
FIG. 7  FIG. 8
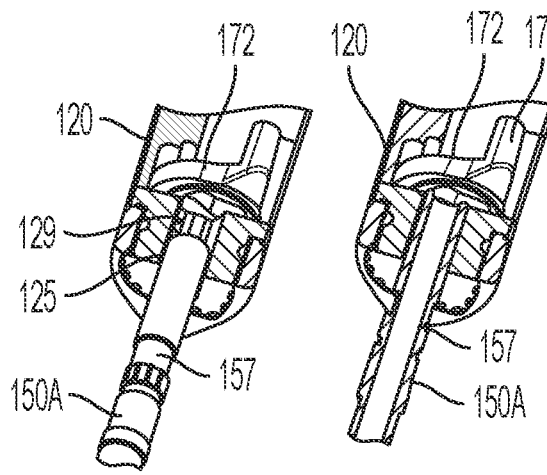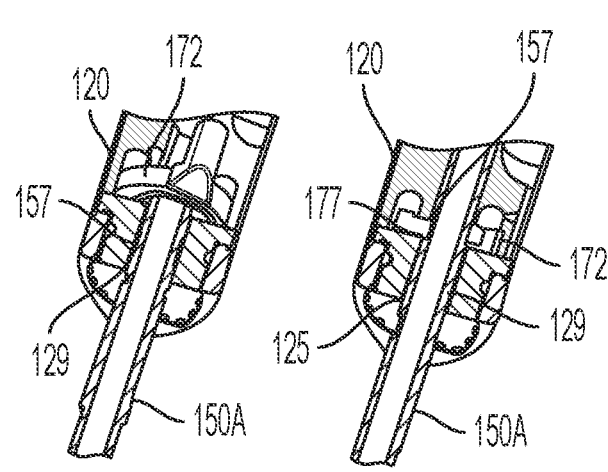
FIG. 9A  FIG. 9B  FIG. 9C  FIG. 9D

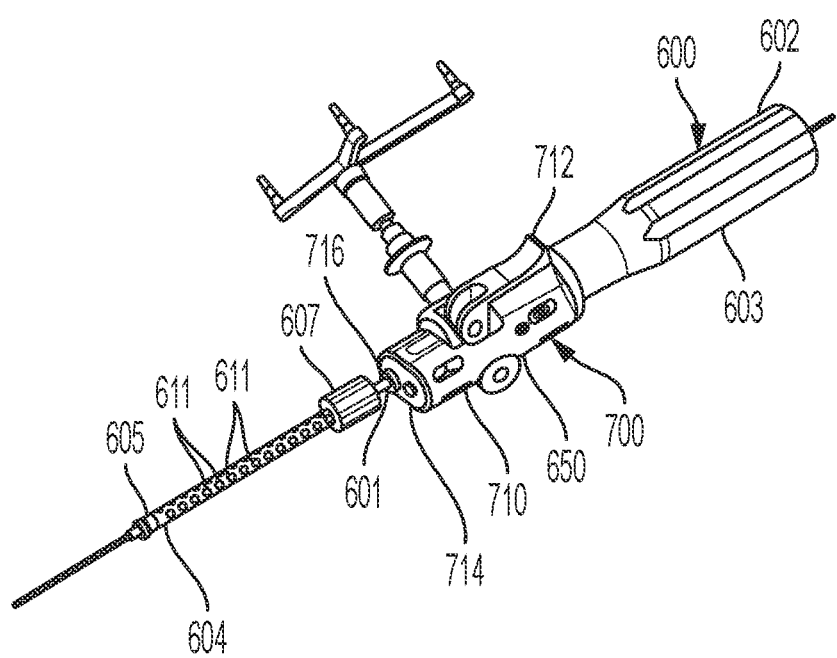
FIG. 33
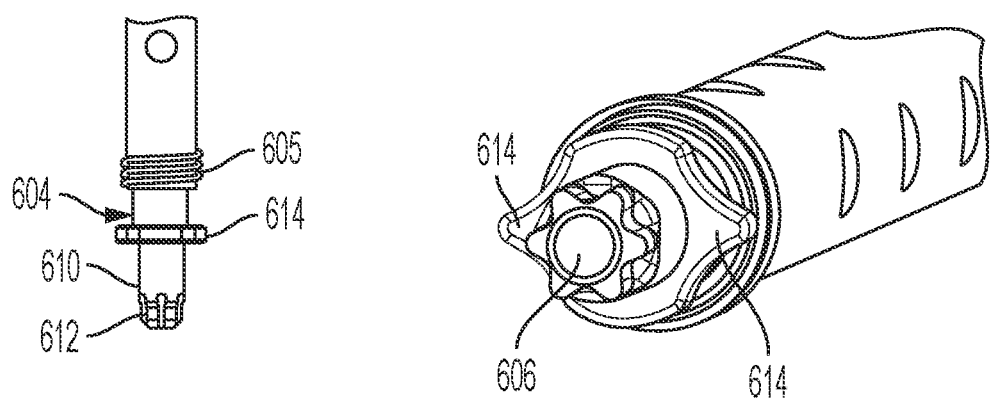
FIG. 34
FIG. 35

SURGICAL INSTRUMENTATION FOR FIXATION OF CERVICAL SPINE

FIELD

The present disclosure relates generally to spinal fixation, and more specifically to surgical instruments used for fixation of the cervical spine.

BACKGROUND

Spinal fusion is a procedure in which damaged vertebrae are removed, and vertebrae adjacent to the removed vertebrae are fused together with graft material. The spine must be immobilized during fusion. To immobilize the spine, one or more fixation rods are anchored to the vertebrae to limit movement.

Fixation rods are anchored to vertebrae using bone screws that are driven into the vertebrae. Before a bone screw is driven into a vertebral body, a hole is prepared in the vertebral body in a minimally invasive manner. In one possible procedure, a drill tube is passed through a small incision and navigated to a desired entry point on the vertebral body. A cortical punch is then advanced through the tube to punch a start hole in the cortical layer of bone. The cortical punch is then removed from the tube, and a drill bit is advanced through the tube to the start hole. Once the drill bit is aligned with the start hole, the surgical drill is powered on to drill a hole of a desired diameter and depth. After the screw hole is drilled, the drill guide is removed, and a bone screw can be driven into the screw hole.

When drilling a screw hole, the depth of drilling must be carefully controlled to ensure that the drill bit does not penetrate too far into the vertebral body. One option for control drill depth is to attach some type of drill stop on the drill tube to limit how far the tip of the drill bit extends past the end of drill tube in the patient. This option may be difficult to implement, however, if there are multiple drill bits and drill tubes of different sizes that must be accommodated.

Guiding drill bits to the proper location can be difficult. Therefore, some drill bits have passages that allow the drill bits to be passed over a Kirschner wire or "K-wire". A K-wire can be attached to a bone at a desired location to precisely navigate the drill bit and other instruments to that location. Although K-wires are helpful for navigation, they present a number of challenges when other instruments are used around them.

SUMMARY

The aforementioned challenges are addressed in many respects by instruments in accordance with the present disclosure.

BRIEF DESCRIPTION OF THE DRAWING FIGURES

The foregoing summary and the following detailed description will be better understood in conjunction with non-limiting examples shown in the drawing figures, of which:

FIG. 7 is a truncated perspective view of a drill tube capture mechanism of the universal drill guide system of FIG. 1, showing the drill tube capture mechanism in a first position;

FIG. 8 is a truncated perspective view of the drill tube capture mechanism of the universal drill guide system of FIG. 1, showing the drill tube capture mechanism in a second position;

FIG. 9A is a truncated perspective view of the drill tube capture mechanism of the universal drill guide system of FIG. 1 during a first step of inserting a drill tube;

FIG. 9B is a truncated perspective view of the drill tube capture mechanism of the universal drill guide system of FIG. 1 during a second step of inserting a drill tube;

FIG. 9C is a truncated perspective view of the drill tube capture mechanism of the universal drill guide system of FIG. 1 during a third step of inserting a drill tube;

FIG. 9D is a truncated perspective view of the drill tube capture mechanism of the universal drill guide system of FIG. 1 after a final step of inserting a drill tube;

FIG. 33 is a perspective view of a bone screw driver with K-wire retention module according to another aspect of the present disclosure, with the bone screw driver and K-wire retention module passed over a K-wire;

FIG. 34 is an enlarged truncated side view of a distal end of the bone screw driver of FIG. 33;

FIG. 35 is an enlarged truncated perspective view of the distal end of the bone screw driver of FIG. 33;

DETAILED DESCRIPTION

The following section describes different instruments used for fixation of the cervical spine according to the present disclosure.

Universal Drill Guide System

Figure 1:
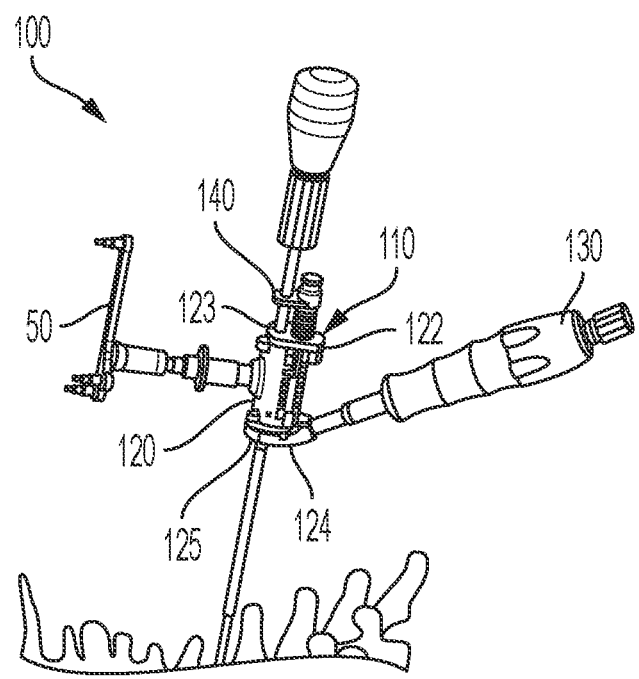
FIG. 1 is a perspective view of a universal drill guide system according to one aspect of the present disclosure.
Figure 2:
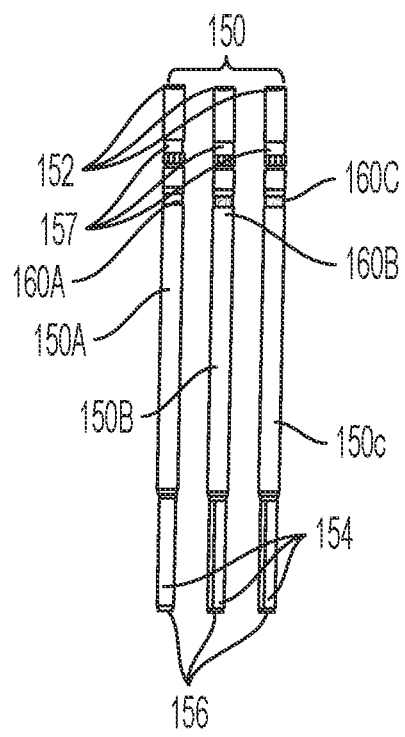
FIG. 2 is a front view of a set of drill tubes for use with the universal drill guide system of FIG. 1.
Figure 3:
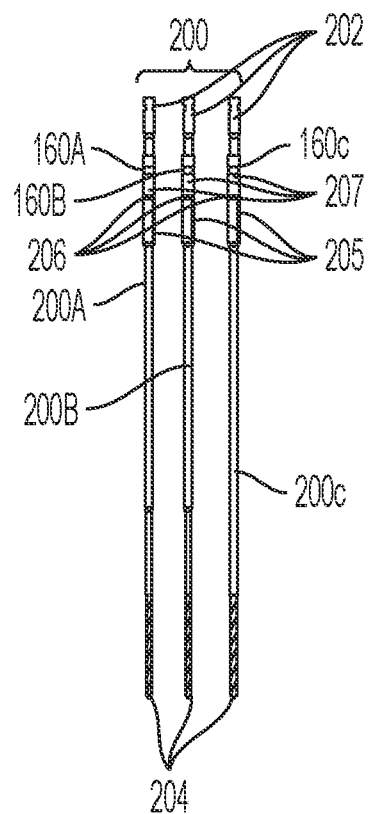
FIG. 3 is a front view of a set of drill bits for use with the universal drill guide system of FIG. 1.

Referring to FIGS. 1-3, a universal drill guide system 100 is shown according to one example. Universal drill guide system 100 features a universal drill guide 110. Universal drill guide 110 includes a tubular guide body 120 and a handle 130 that extends obliquely from the guide body. Guide body 120 has a proximal end 122 defining a proximal opening 123 for receiving a drill bit, as will be described. Guide body 120 also has a distal end 124 defining a distal opening 125 for receiving a drill tube, as will be described. Furthermore, guide body 120 features a drill stop 140 that limits drilling depth by limiting how far a drill bit is advanced through the guide body. An optional navigation star unit 50 is attached to universal drill guide 110 in FIG. 1, which can be calibrated and used with conventional navigation systems.

Universal drill guide system 100 also includes a set of interchangeable drill tubes 150 and a set of interchangeable drill bits 200. The set of interchangeable drill tubes 150 includes a first drill tube 150A, second drill tube 150B, and third drill tube 150C. The set of interchangeable drill bits 200 includes a first drill bit 200A, a second drill bit 200B and a third drill bit 200C. All of the drill tubes 150A, 150B and 150C, and all of the drill bits 200A, 200B and 200C are connectable to universal drill guide 110.

First, second and third drill bits 200A, 200B and 200C are cannulated and have features designed to retain a K-wire, as will be explained in the next section of this description. First, second and third drill bits 200A, 200B and 200C also have different drilling diameters. Each drilling diameter is configured to drill a screw hole of a specific size into a vertebral body. First, second and third drill bits 200A, 200B and 200C each have a proximal end 202 for attachment to a drill driver and an opposite distal end 204 with cutting edges to drill a hole. First, second and third drill bits 200A, 200B and 200C also have a reduced diameter section 205 adjacent an enlarged diameter section 207, forming an abrupt transition. This abrupt transition forms a stop surface 206 located between proximal end 202 and distal end 204. Stop surfaces 206 cooperate with drill stop 140 on guide body 120 to limit how far the drill bits can be advanced into the vertebral body during drilling. Stop surfaces 206 also play a role in removing the drill bits 200A, 200B and 200C after a drilling operation, as will be explained in another section.

First, second and third drill tubes 150A, 150B and 150C are designed to guide the advancement of first, second and third drill bits 200A, 200B and 200C, respectively, during drilling. First, second and third drill tubes 150A, 150B and 150C also keep first, second and third drill bits 200A, 200B and 200C axially stable during drilling. Each of the first, second and third drill tubes 150A, 150B and 150C has a proximal end 152 for attachment to guide body 120 and an opposite distal end 154 that is inserted into the patient at the drilling location. Proximal end 152 of each drill tube 150A, 150B and 150C includes a notch 157 that facilitates attachment to guide body 120, as will be described in more detail.

First, second and third drill tubes 150A, 150B and 150C define drill bit passages 156 having inner diameters specially sized to receive first, second and third drill bits 200A, 200B and 200C, respectively. Thus, first, second and third drill bits 200A, 200B and 200C are designed to only work with first, second and third drill tubes 150A, 150B and 150C, respectively. Indicia are provided on each of first, second and third drill tubes 150A, 150B and 150C, and each of first, second and third drill bits 200A, 200B and 200C, to assist the user in selecting the proper drill tube for the selected drill bit. Any type of indicia can be used. In system 100, first drill tube 150A and first drill bit 200A have matching indicia 160A, second drill tube 150B and second drill bit 200B have matching indicia 160B, and third drill tube 150C and first drill bit 200C have matching indicia 160C. Indicia 160A, 160B and 160C are unique and different from one another, and appear in the form of different colored bands around the circumference of each drill tube and drill bit.

Figure 4:
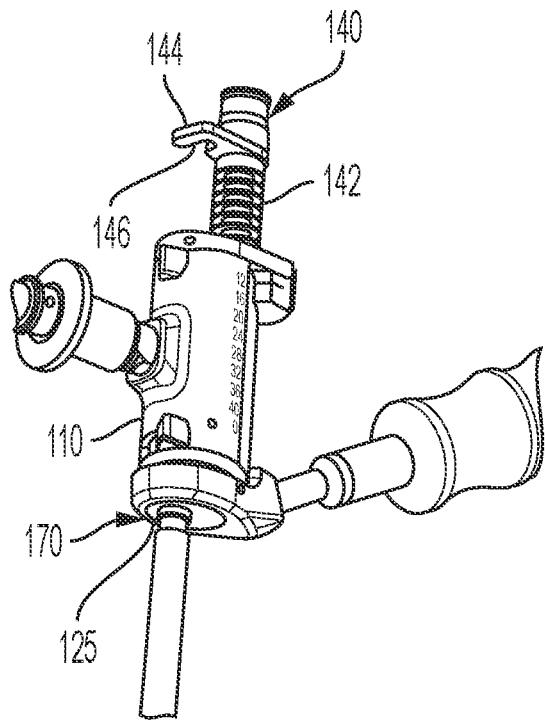
FIG. 4 is a truncated perspective view of the universal drill guide system of FIG. 1.

Referring to FIG. 4, drill stop 140 has a shaft 142 and a stop plate 144 extending laterally from the shaft. Stop plate 144 has a slot 146 having a slot dimension that is wide enough to permit passage of the distal sections of first, second and third drill bits 200A, 200B and 200C through the stop plate. Slot 146 is smaller than the cross sectional dimension of stop surfaces 206 of first, second and third drill bits 200A, 200B and 200C. In this arrangement, stop plate 144 is configured to permit advancement of each of first, second and third drill bits 200A, 200B and 200C through the stop plate up until their respective stop surfaces 206 abut the stop plate. At such time, the drill bit has reached the selected drill depth, and further advancement of the drill bit through guide body 120 is prevented.

Figures 5, 6:
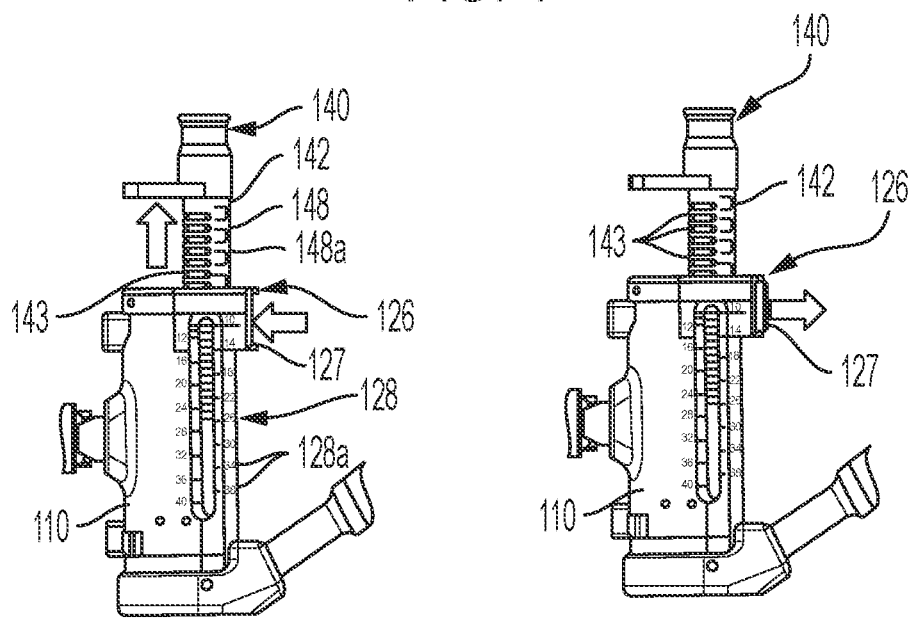
FIG. 5 is a truncated side view of the universal drill guide system of FIG. 1, showing a spring loaded lock in a first state.
FIG. 6 is a truncated side view of the universal drill guide system of FIG. 1, showing the spring loaded lock in a second state.

Referring to FIGS. 5 and 6, drill stop 140 can be raised or lowered to set a desired drilling depth setting. A spring loaded lock 126 releasably engages shaft 142 of drill stop 140 to lock and unlock the shaft. Shaft 142 has a series of circumferential grooves 143 in one side. Spring loaded lock 126 is configured to engage one of grooves 143 to lock the position of shaft 142 under a spring bias. Spring loaded lock 126 includes a release button 127 that can be pressed inwardly as shown in FIG. 5. Pressing release button 127 inwardly disengages spring loaded lock 126 from shaft 142 so the shaft can be raised or lowered relative to guide body 120 to set the depth setting. Once the depth setting is set, release button 127 is released as shown in FIG. 6 to allow spring loaded lock 126 to engage shaft 142 under spring bias. Engagement of spring loaded lock 126 with shaft 142 locks the vertical position of the shaft relative to guide body 120 and fixes the depth setting.

Universal drill guide 110 includes two sets of indicia on the exterior that provide the user with a visual indicator of the selected depth setting. A first set of indicia 128 include a vertical series of markings 128a on the side of guide body 120. A second set of indicia 148 include a vertical series of markings 148a on shaft 142. Each marking 128a, 148a is labeled with a unique number corresponding to a depth in millimeters or other unit of measure. Markings 128a are oriented on a different side of universal drill guide 110 than markings 148a. This placement of redundant markings on two different sides addresses situations where the surgeon can only see one side of universal drill guide 110.

Guide body 120 includes an auto drill tube capture 170 that allows each of first, second and third drill tubes 150A, 150B and 150C to be connected to distal opening 125 in a quick-connect coupling. Auto drill tube capture 170 allows a user to insert one of the drill tubes 150A, 150B and 150C into guide body 120 and lock it in place without touching any locking mechanisms on the guide body. The drill tube is simply inserted into distal opening 125 until it engages an automatic lock. Each of the drill tubes 150A, 150B and 150C has a different inner diameter to accommodate one of the drill bits, as noted above. However, all of the drill tubes 150A, 150B and 150C have the same outer dimensions that engage the drill stop 140 and auto drill tube capture 170. Therefore, all of the drill tubes 150A, 150B and 150C interact with the auto drill tube capture 170 the same way.

Referring to FIGS. 7 and 8, auto drill tube capture 170 includes a spring loaded locking ring 172 inside guide body 120. Locking ring 172 is configured to snap into notches 157 formed in each drill tube 150A, 150B and 150C. Locking ring 172 is rotatable in the guide body between a locking orientation and a release orientation. A pair of compression springs 174 exert a counterclockwise biasing force on locking ring 172 to bias the locking ring in the locking orientation. Each compression spring 174 bears against a locking tab 176 that extends in a proximal direction or upwardly from the rest of locking ring 172.

Locking tabs 176 and compression springs 174 are captive in a pair of slots 178. One end of each compression spring 174 bears against an end wall 179 of a slot 178, and the opposite end of the spring bears against a locking tab 176. In this arrangement, the locking ring 172 is maintained in the locking orientation unless the user manually rotates the locking ring to the release orientation. Locking ring 172 can be rotated by exerting a clockwise force on a switch 173 that is attached to the locking ring. Switch 173 extends through an elongated aperture 121 in guide body 120 and is exposed on the exterior of the guide body.

When locking ring 172 is in the locking orientation, shown in FIG. 7, the compression springs 174 have released energy to push the locking tabs 176 in a counterclockwise direction in their respective slots 178 to rotate the locking ring counterclockwise. When the locking ring 172 is in the release orientation, shown in FIG. 8, the locking tabs 176 are rotated in a clockwise direction to compress the compression springs 174 in their respective slots 178 under stored energy. The user can move the locking ring 172 from the locking orientation to the release orientation by manually rotating the switch 173 in the clockwise direction.

FIGS. 9A-9D show a sequence in which a drill tube, in this example drill tube 150A, is inserted into guide body 120 and locked in place by locking ring 172. The same sequence occurs when drill tube 150B and drill tube 150C are inserted into guide body 120.

Drill tube 150A is inserted through distal opening 125 and into a passage 129 formed in guide body 120, as shown in FIG. 9A. Locking ring 172 is initially disposed in the locking orientation. Drill tube 150A is advanced into passage 129 until it enters locking ring 172, as shown in FIG. 9B. As drill tube 150A continues to advance, the drill tube contacts an interior surface of locking ring 172, as shown in FIG. 9C. This contact between drill tube 150A and locking ring 172 causes the locking ring to rotate out of the locking orientation. Contact with locking ring 172 occurs at a chamfer 177 on the locking ring that extends into passage 129. The proximal end and sidewall of drill tube 150A contact chamfer 177 as the drill tube is advanced proximally in the passage 129. The orientation of the chamfer 177 is such that the side wall of the drill tube 150A deflects the locking ring a small distance in a counterclockwise direction against the bias of the compression springs, storing additional energy in the springs. This deflection begins in FIG. 9B and continues in FIG. 9C.

As drill tube 150A is advanced further into passage 129, the locking ring 172 remains deflected until the notch 157 in the drill tube aligns with the chamfer 177, shown in FIG. 9D. When this alignment occurs, the force deflecting the locking ring 172 is temporarily released, allowing the compression springs 174 to expand and return to their relaxed state. This expansion causes locking ring 172 to rotate back toward the locking orientation. Chamfer 177 snaps radially inwardly into the notch 157 under the bias of the compression springs 175. The axial dimension of the locking ring 172 is substantially equal to the axial dimension of the slot 157, such that the axial position of the drill tube is fixed and locked in the guide body 120.

Figure 10:
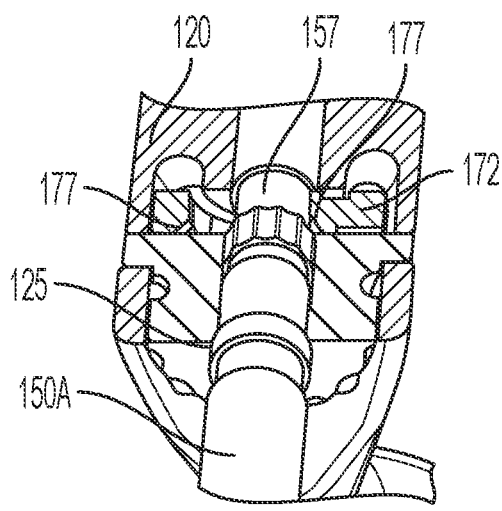
FIG. 10 is an enlarged truncated perspective view of the drill tube capture mechanism of the universal drill guide system of FIG. 1 in a locking orientation.
Figure 11:
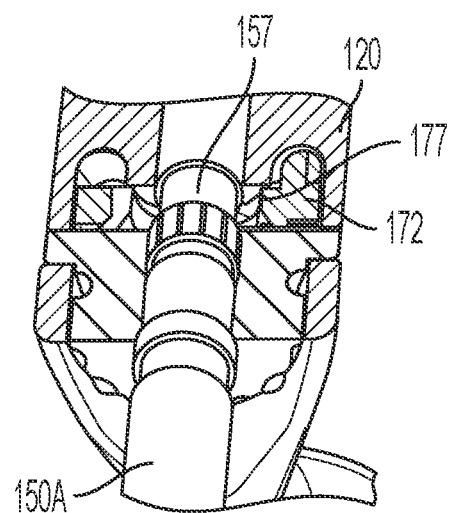
FIG. 11 is an enlarged truncated perspective view of the drill tube capture mechanism of the universal drill guide system of FIG. 1 in a release orientation.

FIG. 10 shows a cross section showing locking ring 172 in the locking orientation. The portion of the locking ring 172 that engages notch 157 is circled. FIG. 11 shows a cross section showing locking ring 172 in the release orientation. In this condition, no portion of locking ring 172 extends into notch 157. As can be appreciated from these two Figures, drill tube 150A can be removed from guide body 120 by rotating the switch 173 in the counterclockwise direction against the bias of the compression springs. This rotation moves the chamfer 177 out of the notch 157, as shown in FIG. 11. In this state, the drill tube is no longer axially restrained by the locking ring 172 and can be pulled out of the guide body 120.

Drill bits 200A, 200B and 200C each have an outer diameter that corresponds to the inner diameter of drill tubes 150A, 150B and 150C, respectively. Each of drill bits 200A, 200B and 200C is long enough to extend from above drill stop 140 to beyond the distal end of the drill tube when the drill tube is attached to guide body 120.

Figure 12:
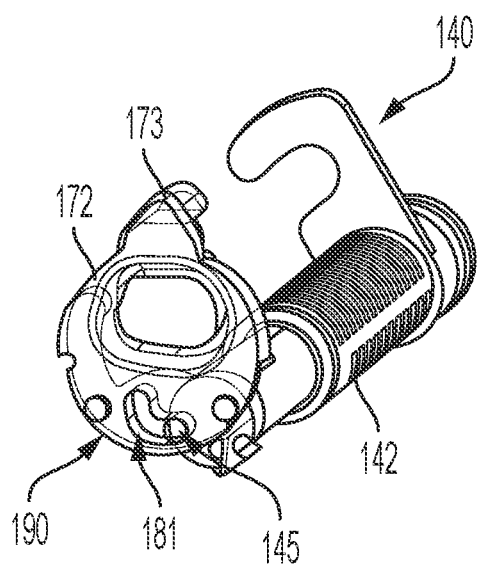
FIG. 12 is an enlarged perspective view of components of the universal drill guide system of FIG. 1, showing the components when the drill stop is in a position for engagement with a drill.
Figure 13:
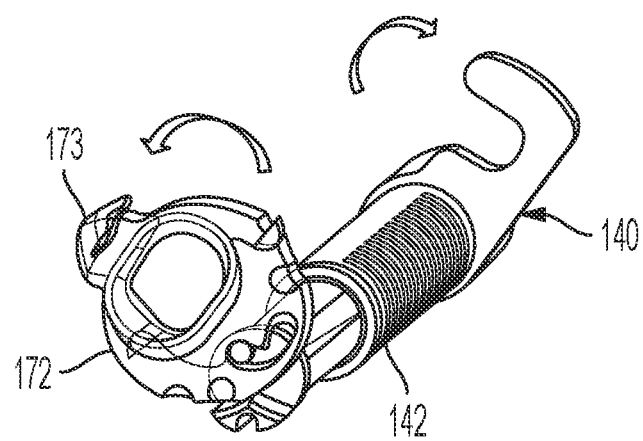
FIG. 13 is an enlarged perspective view of components of the universal drill guide system of FIG. 1, showing the components when the drill stop is in a position released from a drill.

After drilling is completed, it is sometimes necessary to remove the drill driver and universal drill guide 110 from the operating site while leaving the drill tube and drill bit in place. This can be a technical challenge, because the drill stop 140 is engaged with the drill bit as shown in FIG. 1. Therefore, the universal drill guide 110 includes a mechanism that pivots the drill stop 140 counterclockwise and away from the drill bit as the universal drill guide is released from the drill tube. This is accomplished with a camming mechanism 190 that interconnects the locking ring 172 with the shaft 142 of the drill stop 140, as shown in FIGS. 12 and 13.

Locking ring 172 includes a cam slot 181 that drives a cam following pin 145 at the bottom of the shaft 142. With this arrangement, rotation of the locking ring 172 clockwise (or left in the Figures) causes the shaft 142 and drill stop 140 to simultaneously rotate counterclockwise (or right in the Figures), moving the drill stop 140 away from the drill bit so that the universal drill guide 110 can be lifted off of the drill tube while the drill tube and drill bit remain in the patient. The process of lifting universal drill guide 110 off of drill tube 150A is illustrated in FIGS. 14 and 15.

Figure 14:
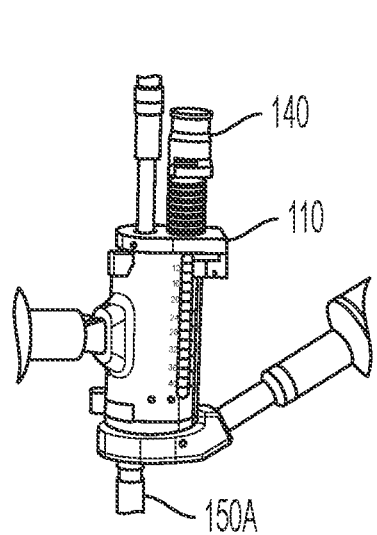
FIG. 14 is an truncated perspective view of the universal drill guide system of FIG. 1, showing the universal drill guide system in a condition to be detached from a drill tube.
Figure 15:
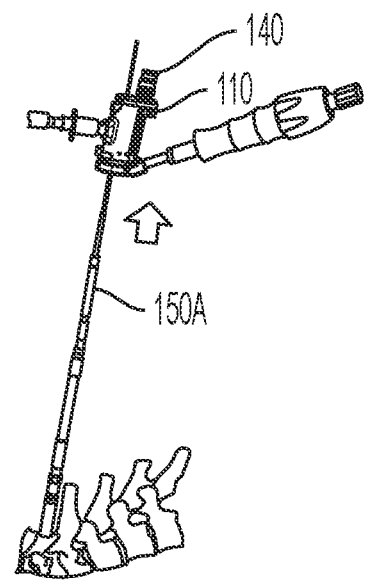
FIG. 15 is another truncated perspective view of the universal drill guide system of FIG. 1, showing the universal drill guide system being detached from the drill tube.

It can be seen in FIG. 14 that the switch 173 on the locking ring 172 is rotated clockwise or to the left. This pivots the drill stop 140 counterclockwise or to the right. disengaging the drill stop from drill bit 200A, so that universal drill guide 110 can be lifted off of drill tube 150A and the drill bit without being inhibited, as shown in FIG. 15.

Cannulated Drill with K-Wire Retention

First, second and third drill bits 200A, 200B and 200C are cannulated and have features designed to retain a K-wire, as described previously. Drill bits 200A, 200B and 200C are generally the same, but have a few differences. The outer diameters of drill bits 200A, 200B and 200C are different, with each outer diameter configured to drill a hole of a different size. The inner diameter of drill bit 200A is smaller than the inner diameters of drill bits 200B and 200C, with the inner diameter of drill bit 200A configured to allow a K-wire having a diameter of 1.0 mm to pass through the bit. The inner diameters of drill bits 200B and 200C are larger, each configured to allow a K-wire having a diameter of 1.5 mm to pass through the bit. Drill bits 200A, 200B and 200C also have different colored indicia on their exterior to assist the user in pairing each drill bit with its corresponding drill tube.

Figure 16:
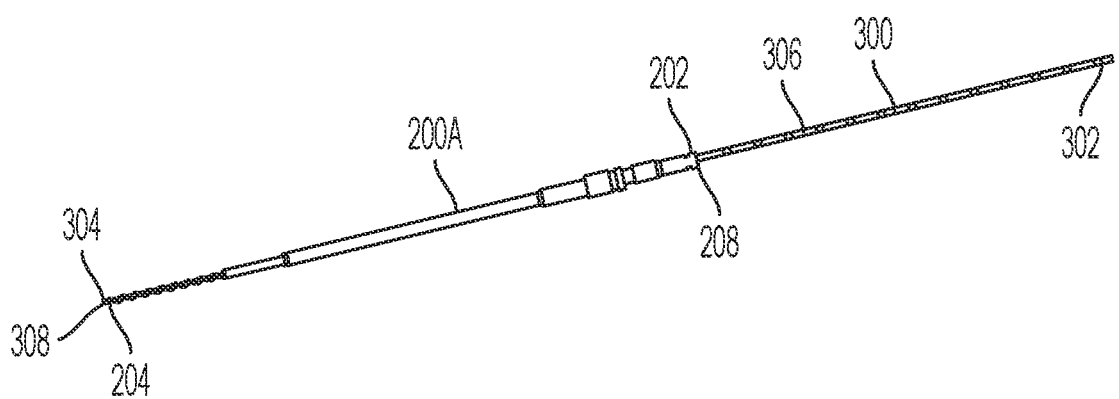
FIG. 16 is a perspective view of a cannulated drill bit and K-wire according to another aspect of the present disclosure.

Referring now to FIG. 16, drill bit 200A will be described in more detail, with the understanding that the same description applies to drill bits 200B and 200C. Drill bit 200A is shown with a K-wire 300. K-wire 300 extends through a passage 208 that extends through drill bit 200A from proximal end 202 to distal end 204. K-wire 300 has a proximal end 302, a distal end 304 and wire body 306 extending between the proximal and distal ends. Distal end 304 has a sharp pointed end 308 that can be punched into bone at a selected location. Once K-wire 300 is punched into the bone, a surgeon can pass a cannulated bone screw, drill bit, or other instrument over the K-wire and advance it to the selected location to perform an operation.

K-wire 300 is significantly longer than drill bit 200A. Therefore, K-wire 300 can extend through drill bit 200A with proximal end 302 of the K-wire projecting proximally and outside of proximal end 202 of the drill bit. At the same time, K-wire 300 can extend through drill bit 200A with distal end 304 of the K-wire projecting distally and outside of distal end 204 of the drill bit. K-wire 300 is releasably securable inside in drill bit 200A as an assembly that allows the K-wire and drill bit to be drilled into a bone together.

Figure 17:
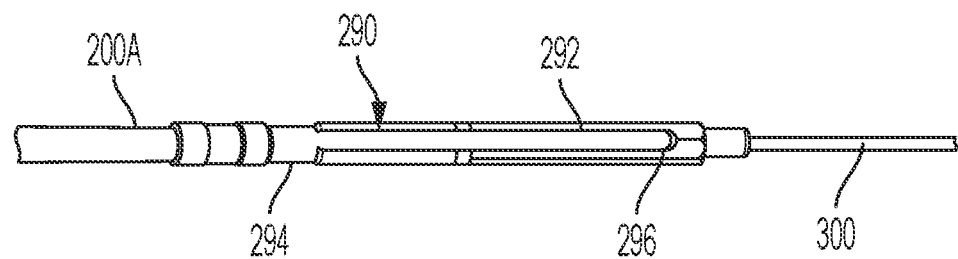
FIG. 17 is an enlarged truncated view of a cannulated drill bit and K-wire according to another aspect of the present disclosure.
Figure 18:
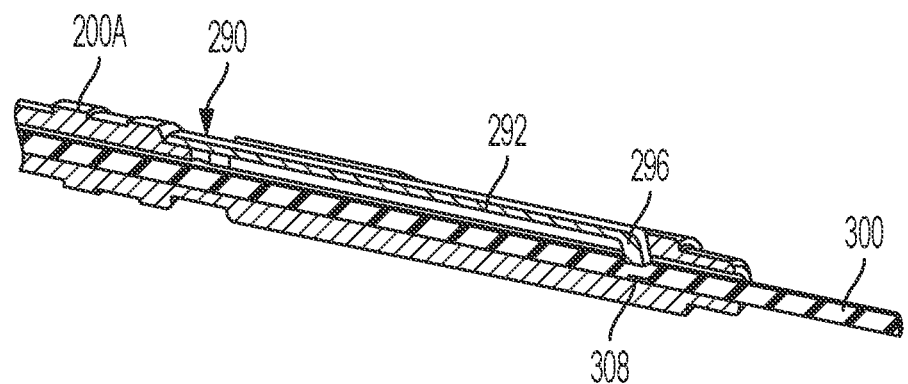
FIG. 18 is an enlarged truncated cross section view of the cannulated drill bit and K-wire of FIG. 17.

Referring to FIGS. 17 and 18, K-wire 300 is releasably secured to the inside of drill bit 200A during drilling by a retention mechanism 290 that is built into the drill bit. Retention mechanism 290 is configured to engage K-wire 300 to prevent axial advancement of the K-wire relative to drill bit 200A during drilling. This retention ensures that K-wire 300 and drill bit 200A are inserted together and advance the same amount into bone. Retention mechanism 290 also allows torque applied to drill bit 200A to be transferred to K-wire 300. Thus, K-wire 300 and drill bit 200A rotate in unison when the retention features are engaged. A torque driver can apply torque to K-wire 300 and drill bit 200A in unison to plant the K-wire in the bone and form a pilot hole for a bone screw. Once the pilot hole is drilled, drill bit 200A can be disengaged from K-wire 300 and removed from the patient while leaving the K-wire in the bone.

Retention mechanism 290 includes a retention clip 292 configured to releasably engage with a locking groove 308 on an exterior portion of K-wire 300. Locking grooves and retention clips according to the present disclosure can have various forms and geometries. For example, the locking groove can extend around a portion of the K-wire, or completely surround the K-wire in a circumferential manner. The retention clip can be clipped onto the exterior of the drill bit, or be formed integrally with the drill bit. The retention clip can also have an inward-extending retention end that can be pressed into the locking groove to limit axial displacement of the K-wire in the drill bit.

Retention clip 292 has a hub portion 294 that attaches the retention clip to drill bit 200A. Retention clip 292 also has a retention end 296 opposite the hub portion 294. Retention end 296 projects radially inwardly through a sidewall of drill bit 200 to engage locking groove 308 of K-wire 300.

Figure 19:
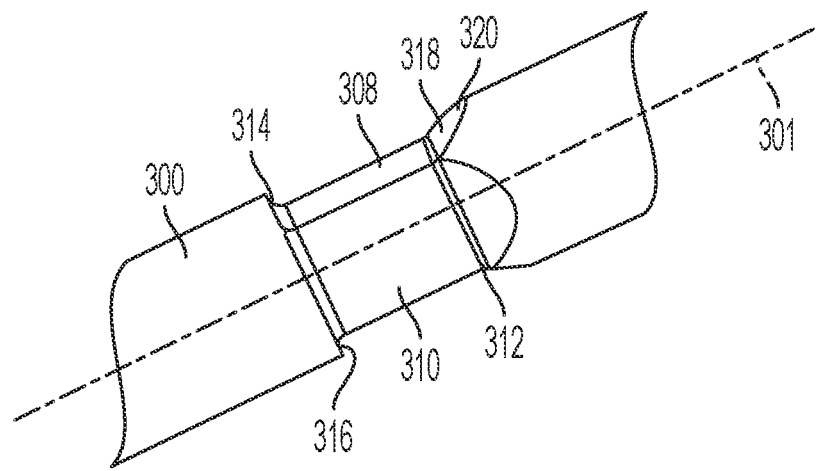
FIG. 19 is an enlarged perspective view of a cannulated drill bit according to another aspect of the present disclosure, showing a midsection of the drill bit.

K-wires according to the present disclosure can have a geometry in the locking groove that allows torque to be transferred from the drill bit/retention clip to the K-wire. For example, the K-wire can have a flat surface on a portion of its exterior in the groove that engages a flat edge on the retention end of the retention clip. FIG. 19 shows an example of a K-wire 300 with a locking groove 308 that has a four-sided square-shaped section 310 in the groove. K-wire 300 can work with a retention clip formed in a drill bit according to any of the previous examples, such as drill bit 200A.

Locking grooves according to the present disclosure can be bounded by a proximal end wall and a distal end wall. The proximal and distal end walls can have different geometries that control axial displacement of the K-wire relative to the surrounding drill bit. In the example in FIG. 19, locking groove 308 has a proximal end wall 312 and a distal end wall 314. Distal end wall 314 is substantially perpendicular to a longitudinal axis 301 of K-wire 300. This forms a stop 316 that can abut the retention end 296 of retention clip 292 when the retention clip is engaged in the locking groove 308, thereby preventing relative displacement of K-wire 300 in the distal direction. In contrast to the distal end wall 314, the proximal end wall 312 consists of inclined surfaces 318 extending at an acute angle relative to axis 301. The inclined surfaces 318 form a ramped section 320 that allows retention end 296 of retention clip 292 to gradually deflect outwardly and slide out of locking groove 308 during withdrawal of drill bit 200A from the K-wire 300 after drilling is completed.

Retention clip 292 is operable in a locked mode and a released mode. In the locked mode, the retention end 296 is pressed and held inwardly in the locking groove, as shown in FIG. 18. This locks the axial position of K-wire 300 relative to the drill bit 200 during drilling. After drilling is complete, the inward force on the retention end 296 can be removed, leaving the retention clip 292 in the released mode. In the released mode, it is possible to move the drill bit 200 in a proximal direction relative to the K-wire 300 until the drill bit is completely removed from the K-wire. This allows drill bit 200A to be withdrawn from a patient while leaving the K-wire 300 in the patient for further use.

Figure 20:
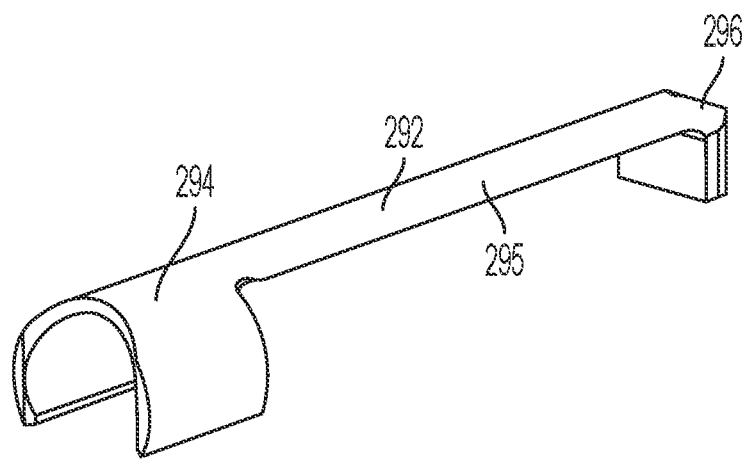
FIG. 20 is an enlarged perspective view of a component of a cannulated drill bit according to another aspect of the present disclosure.

Referring to FIG. 20, retention clip 292 has a partially-cylindrical hub portion 294 configured to clip onto the rounded exterior of a drill bit, similar to a pocket clip on a pen. Retention clip 292 also has a flexible arm 295 between hub portion 294 and a retention end 296. Flexible arm 295 allows retention end 296 to flex radially outwardly under stored energy as the drill bit is withdrawn from the K-wire. The retention end 296 remains deflected in an outward position as the drill bit is removed from the K-wire. Once the drill bit is removed from the K-wire, the retention end 296 snaps back in the radially inward direction to its relaxed state shown in FIG. 20.

Figure 21:
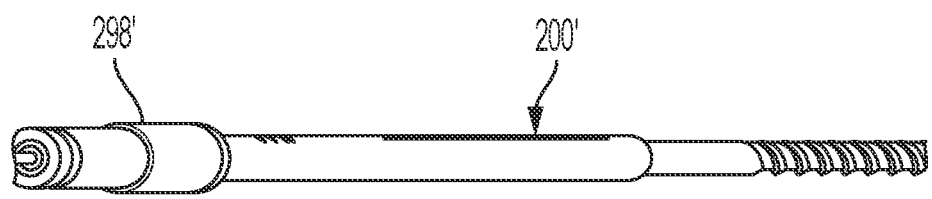
FIG. 21 is a truncated perspective view of a cannulated drill bit and K-wire according to another aspect of the present disclosure, with a force retention sleeve shown in a first position.
Figure 22:
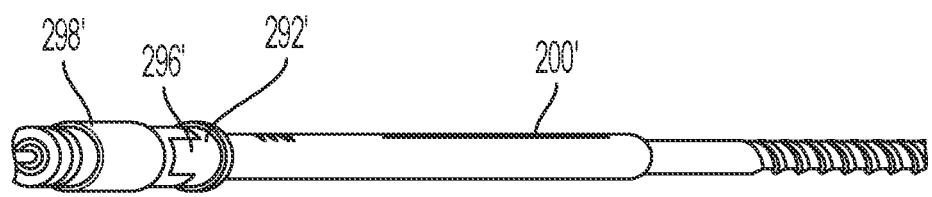
FIG. 22 is a truncated perspective view of the cannulated drill bit and K-wire of FIG. 21, with the force retention sleeve shown in a second position.

Force can be applied to the retention ends of retention clips in a radially inward direction to press and hold the retention clips in the engaged mode with the locking groove. The inward force can be applied in a number of ways. FIGS. 21 and 22 show another example of drill bit 200' with a removable sleeve 298'. Sleeve 298' is slidable over the exterior of drill bit 200' between a first position and a second position. In the first position (FIG. 21), sleeve 298' covers retention end 296' and applies inward force to it to hold retention clip 292' in the engaged mode. In the second position (FIG. 22), sleeve 298' is moved off of retention end 296', allowing the retention end to flex outwardly to permit disengagement of retention clip 298' from the locking groove on a K-wire 300.

Figure 23:
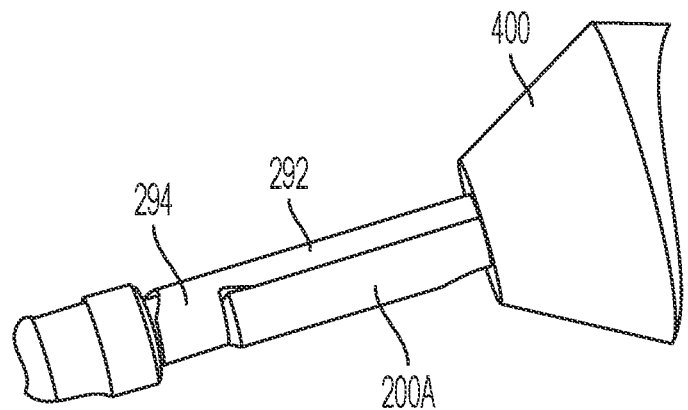
FIG. 23 is an enlarged truncated perspective view of a cannulated drill bit according to another aspect of the present disclosure, with the cannulated drill bit attached to a drill driver.
Figure 24:
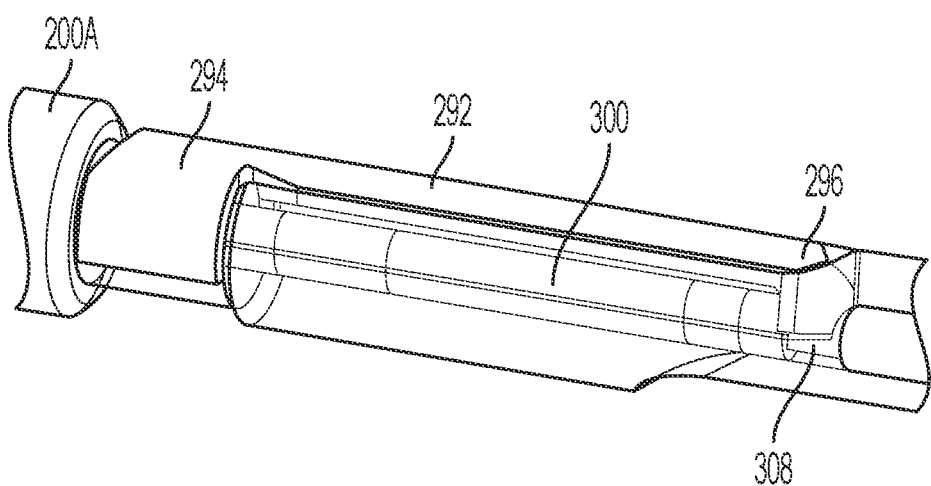
FIG. 24 is another enlarged truncated perspective view of the cannulated drill bit of FIG. 23, with some features shown transparent for clarity.
Figure 25:
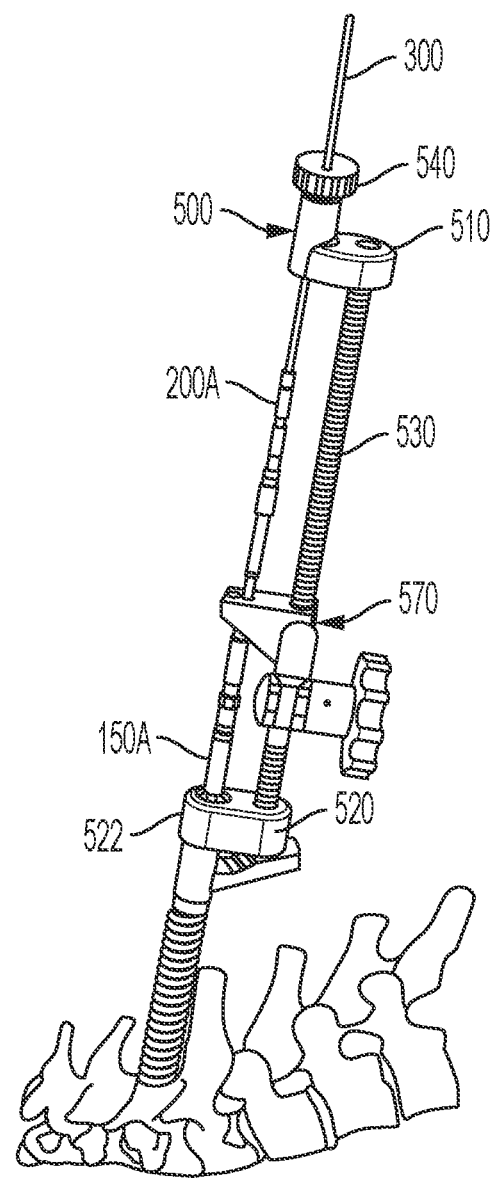
FIG. 25 is a perspective view of a drill removal tool according to another aspect of the present disclosure.
Figure 26:
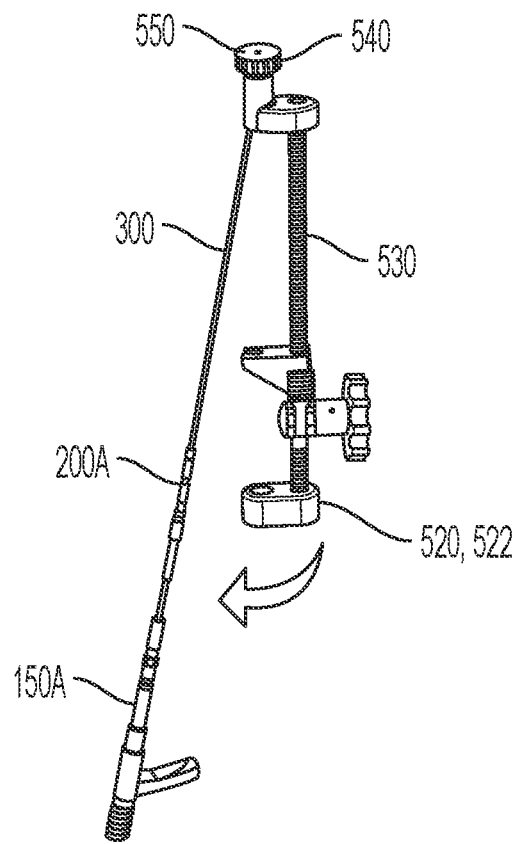
FIG. 26 is a truncated perspective view of the drill removal tool of FIG. 25 during attachment to a cannulated drill bit and K-wire.

In other examples, a separate instrument can be used to lock the retention clip into engagement with the K-wire. FIGS. 23 and 24 show an example in which a retention clip 292 of a drill bit 200A is maintained in the engaged mode by a drill driver 400. Drill driver 400 is clamped over retention end 296 of retention clip 292 and applies external force to maintain the retention clip in the engaged mode in a four-sided locking groove 308 of a K-wire 300.

Drill Removal Tool

Referring to FIGS. 25-32, a drill removal tool 500 is shown according to one example. Drill removal tool 500 is designed to remove a cannulated drill bit from bone after a hole is drilled, while leaving the K-wire in place in the bone. Once the drill bit is removed from the K-wire, a bone screw can be advanced over the K-wire and driven into the screw hole. Drill removal tool 500 can be used with any combination of drill bit, drill tube and K-wire. For purposes of this description, drill removal tool 500 will be described in use with the same drill bit 200A, drill tube 150A and K-wire 300 described previously.

Drill removal tool 500 includes a first support end 510, a second support end 520 and a toothed rack 530 extending between the first support end and second support end. First support end 510 includes a wire clamp 540 operable to clamp onto K-wire 300. Second support end 520 include a C-shaped base 522 configured to fit snugly around drill tube 150A. A drill bit remover 570 is axially displaceable on toothed rack 530 between first support end 510 and second support end 520.

Referring to FIGS. 26-29, wire clamp 540 is configured to be passed over the exposed end of K-wire 300 in an unlocked state, and subsequently clamp the K-wire in a locked state. Clamp 540 includes a hollow housing 542 which extends from first support end 510. Housing 542 defines a clamp passage 544 having a proximal end 546, distal end 548 and a converging section 549 between the proximal and distal ends. Proximal end 546 has an internal thread 547. A knob 550 includes a dial 552 and shaft 554 with an external thread 557 that mates with internal thread 547 in clamp passage 544. Knob 550 defines a through bore 558 that axially receives a clamping pin 560. Clamping pin 560 defines a through passage 562 and wedge shaped collet 564 at its distal end 566. Collet 564 has an outer diameter that gradually decreases toward distal end 566, forming a cone-shaped projection that conforms to the shape of converging section 549. Through passage 562 has an inner diameter adapted to receive K-wire 300.

Figure 27:
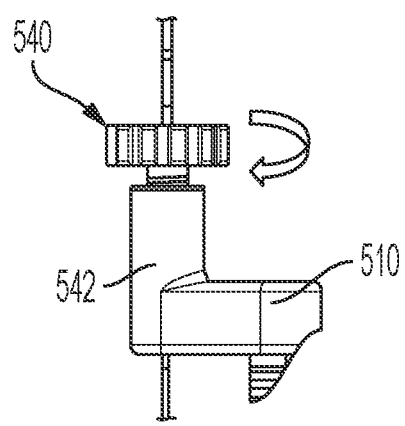
FIG. 27 is a truncated side view of a wire clamp according to another aspect of the present disclosure, showing the wire clamp in an unclamped state.
Figure 28:
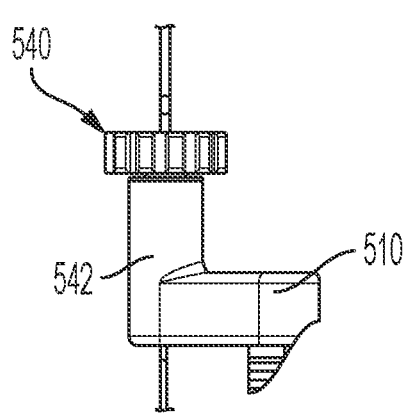
FIG. 28 is a truncated side view of the wire clamp of FIG. 27, showing the wire clamp in a clamped state.
Figure 29:
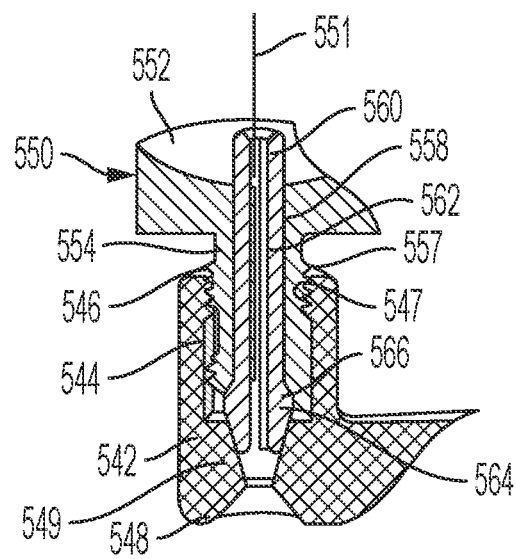
FIG. 29 is an enlarged truncated cross section view of the wire clamp of FIG. 27.

Knob 550 is rotatable about a knob axis 551 between the unlocked state and the locked state. Knob axis 551 aligns coaxially with through bore 558 and through passage 562. FIG. 27 shows knob 550 in the unlocked state, and FIG. 28 shows the knob after it is rotated to the locked state. Internal thread 547 and external thread 557 promote axial displacement of knob 550 when the knob is rotated. Clamping pin 560 is axially fixed in knob 550, with the distal end 556 of the knob abutting collet 564. In this arrangement, knob 550 and clamping pin 560 move axially and in unison in clamp housing 544 when the knob is rotated. Internal and external threads 547, 557 are oriented so that rotation of dial 552 in a clockwise direction CW causes knob 550 and collet 560 to move distally into converging section 549. The tapered shape of converging section 549 exerts inward force on collet 564 as clamping pin 560 moves distally, compressing the collet 564 so that it locks against K-wire 300 in a locked state.

Drill removal tool 500 is attachable over K-wire 300, drill bit 200A and drill tube in two steps. In a first step, wire clamp 540 is passed over K-wire. To pass wire clamp 540 over K-wire 300, knob 550 is rotated counterclockwise to the unlocked state so that collet 564 is not compressed in converging section 549 of clamp passage 544. Once the proximal end of K-wire 300 passes through wire clamp 540, second support end 520 and C-shaped base 522 are pivoted toward drill tube 150A in the direction shown by the curved arrow in FIG. 26. C-shaped base 522 is pivoted until the opening 523 in C-shaped base receives drill tube 150A in a snug fit.

Figure 30:
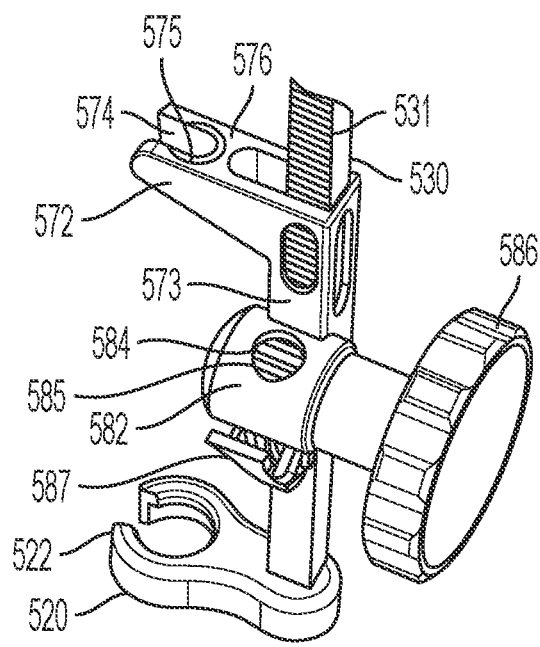
FIG. 30 is a truncated perspective view of components of the drill removal tool of FIG. 25.
Figure 32:
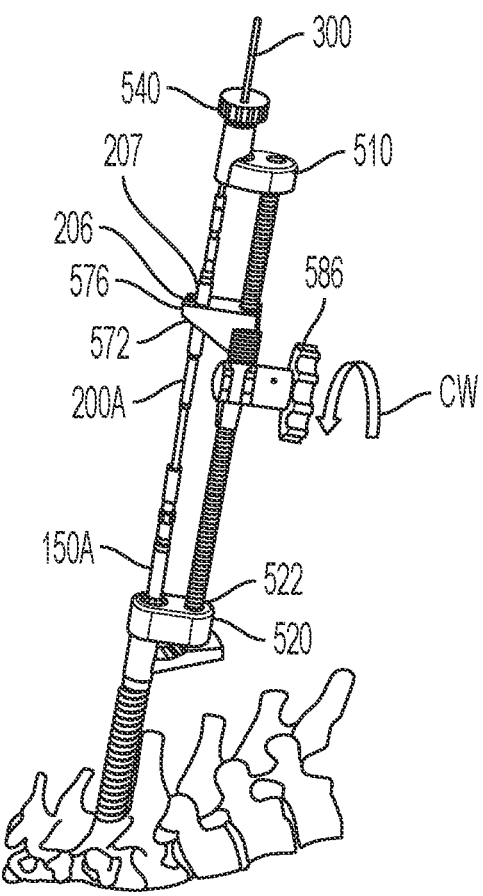
FIG. 32 is another truncated perspective view of the drill removal tool of FIG. 25, shown during removal of the drill bit from the patient.

Referring to FIG. 30, drill bit remover 570 includes a fork-shaped anvil 572 that defines a through slot 574. Through slot 574 aligns with clamp passage 544 and opening 523, forming a straight passage through all three parts of drill removal tool 500. Anvil 572 has a flat fork-lift surface 576 above through slot 574. Through slot 574 and fork-lift surface 576 are configured to engage drill bit 200A beneath stop surface 206, as mentioned earlier. Through slot 574 has a rounded end 575 with a diameter that is slightly larger than reduced diameter section 205 on drill bit 200A, but smaller than enlarged diameter section 207. Therefore, anvil 572 is configured to receive reduced diameter section 205 of drill bit 200A into through slot 574, with fork-lift surface 576 positioned beneath or distally with respect to stop surface 206. In this position, fork-lift surface 576 abuts enlarged diameter section 207 at stop surface 206, as shown in FIG. 32.

Drill bit remover 570 includes a sleeve 573 connected to anvil 572. Sleeve 573 surrounds rack 530 and interconnects anvil 572 with C-shaped base 522. A pinion housing 582 extends from one side of sleeve 573 and contains a pinion 584. Pinion 584 has a plurality of gear teeth 585 that mesh or engage with teeth 531 on rack 530 through an opening between the pinion housing 582 and rack. A wheel handle 586 is attached to pinion 584 and extends outside of pinion housing 582. Wheel handle 586 and pinion 584 are rotatable in unison relative to pinion housing 582. In this arrangement, wheel handle 586 can be rotated to move drill bit remover 570 up or down rack 530.

Figure 31:
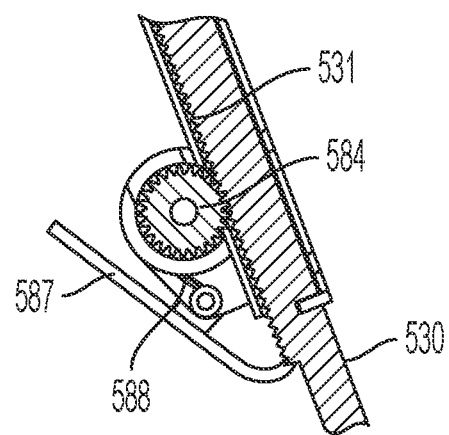
FIG. 31 is another truncated perspective view of components of the drill removal tool of FIG. 25.

Referring to FIGS. 30 and 31, a spring loaded pawl 587 releasably engages teeth 531 on rack 530. Pawl 587 is biased into engagement with teeth 531 by a spring 588. Engagement of pawl 587 with teeth 531 occurs automatically after drill bit remover 570 is displaced along rack 530, and serves to lock the position of the drill bit remover relative to the rack to maintain the position of anvil 572. Pawl 587 is pivotable out of engagement with teeth 531 against the bias of the spring 588 to release the pawl and allow drill bit remover 570 to be moved on the rack. Pawl 587 can be pivoted out of engagement with teeth 531 by depressing a tab 589 that extends from the pawl. If desired, the strength of spring 588 can be designed to hold pawl 587 against rack 530 but allow the pawl to ride along the rack when wheel handle 586 is turned, in the manner of a ratchet. Alternatively, the strength of spring 588 can be selected so that pawl 587 will not disengage from teeth 531 when wheel handle 586 is turned, and only disengage from the teeth when the user depresses tab 589.

Pinion 584 is positioned on the left side of rack 530 when facing wheel handle 586. In this arrangement, rotation of wheel handle 586 in the clockwise direction CW raises anvil 572 upwardly, or toward first support end 510. This causes fork-lift surface 576 to bear upwardly or proximally against stop surface 206 on drill bit 200A, displacing drill bit 200A in the proximal direction. Therefore, to remove drill bit 200A from the patient, without removing K-wire 300, the user first locks wire clamp 540 to axially fix K-wire 300. Then, the user rotates wheel handle 586 clockwise to move drill bit 200A in the proximal direction relative to K-wire 300. This has the effect of withdrawing drill bit 200A from the patient while not displacing K-wire 300 and keeping the K-wire in place. Wheel handle 586 is rotated until distal end 204 of drill bit 200A is removed from the patient. Once drill bit 200A is no longer in the patient, wire clamp 540 is unlocked, and C-shaped base 522 is detached from drill tube 150A. This allows drill removal tool 500 to once again move along K-wire 300. Drill removal tool 500 is then lifted off of K-wire 300, with fork-lift surface 576 supporting drill bit 200A such that the drill bit is also removed from the K-wire. After drill bit removal tool 500 is removed from K-wire 300, drill tube 150A can be removed from the patient, as well any tissue dilators. In the present example, drill tube 150A extends through multiple telescopic dilators, the outermost dilator D being visible in FIG. 32.

In an alternate MIS technique, the drill bit 200A can be drilled into bone without K-wire 300. In such instances, drill removal tool 500 can be used to insert K-wire 300 into the bone through drill bit 200A. To begin this technique, a universal drill guide such as the embodiment previously described is attached to a navigation unit and calibrated. The drill stop height is set and the appropriate drill tube is attached to the universal drill guide. An obturator is then inserted into the universal drill guide and drill tube and locked in place. The universal drill guide and obturator are then probed to the desired drilling position in the patient. The obturator is then removed from the universal drill guide and drill tube, and replaced with a cortical punch. The cortical punch is used to create a start hole in the cortical layer, and then removed. The appropriate drill bit is then attached to a driver, inserted into the universal drill guide, and advanced through the drill tube to drill a hole into the bone. Once the drill bit is drilled into bone, the universal drill guide is detached and removed from the drill tube, leaving the drill bit and drill tube in place.

A tissue dilator D is attached to a dilator handle and advanced over the drill tube until it contacts the tissue surrounding the drill tube. The dilator is then pushed and rotated to dilate tissue. A tissue protector P is then advanced over the dilator. A K-wire can be then be inserted into the bone through the drill bit.

Referring to FIGS. 46-52, one process for inserting a K-wire 300 through drill bit 200A is shown. In a first step, K-wire 300 is loaded into drill removal tool 500. Knob 550 is rotated to an unlocked position, and K-wire 300 is inserted through the knob in the direction shown by the arrow in FIG. 46. K-wire 300 is advanced through knob 550 until a long marking 303 on the K-wire is fully covered by the drill removal tool 500. Once K-wire 300 is advanced through drill removal tool 500 to the appropriate position, knob 550 is rotated to a locked position as shown by the arrow in FIG. 47 to lock the K-wire in the wire clamp 540.

Figure 48:
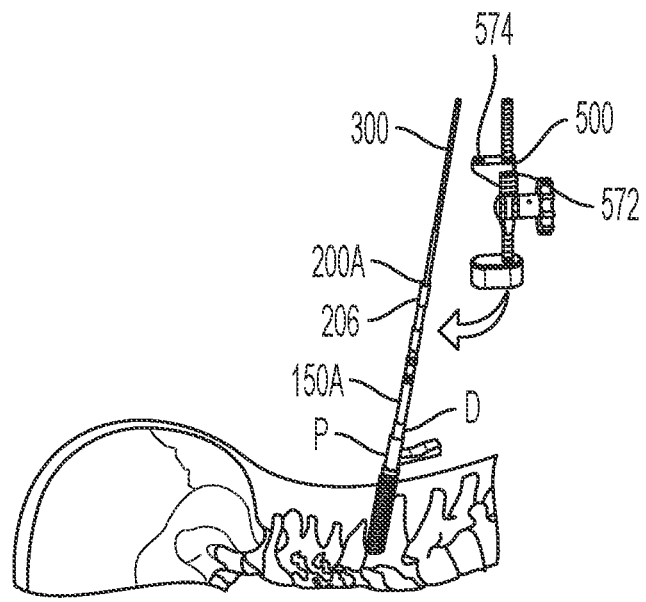
FIG. 48 is another truncated perspective view of the drill removal tool of FIG. 25, showing another step of the alternate technique.
Figure 49:
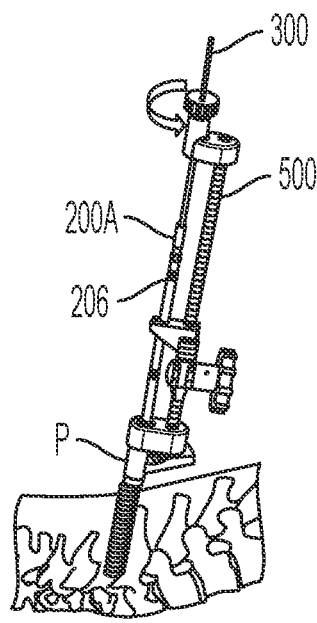
FIG. 49 is another truncated perspective view of the drill removal tool of FIG. 25, showing another step of the alternate technique.

Drill removal tool 500 and K-wire 300 are positioned over the proximal end 202 of drill bit 200A. K-wire 300 is then guided down into drill bit 200A. The bottom portion of drill removal tool 500 is pivoted toward drill bit 200A and dilator D as shown in FIG. 48 until the drill bit is received in through slot 574 of anvil 572. Drill removal tool 500 is pivoted while making sure that anvil 572 is positioned beneath stop surface 206. Once drill removal tool 500 is mounted to drill bit 200A and dilator D, knob 550 is rotated to the unlocked position in the direction shown in FIG. 49.

Figure 50:
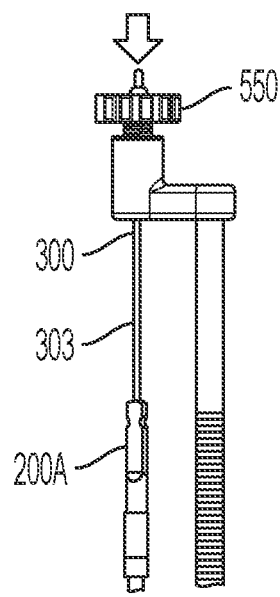
FIG. 50 is another enlarged truncated perspective view of the drill removal tool of FIG. 25, showing another step of the alternate technique.
Figure 51:
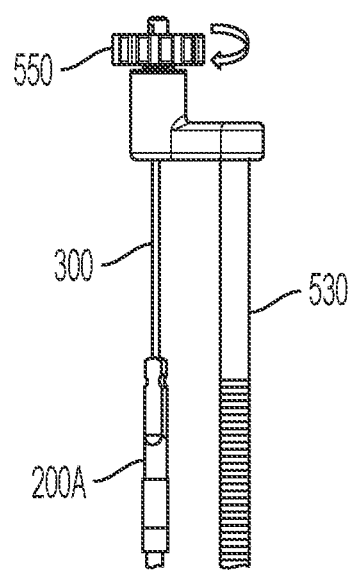
FIG. 51 is another enlarged truncated perspective view of the drill removal tool of FIG. 25, showing another step of the alternate technique.
Figure 52:
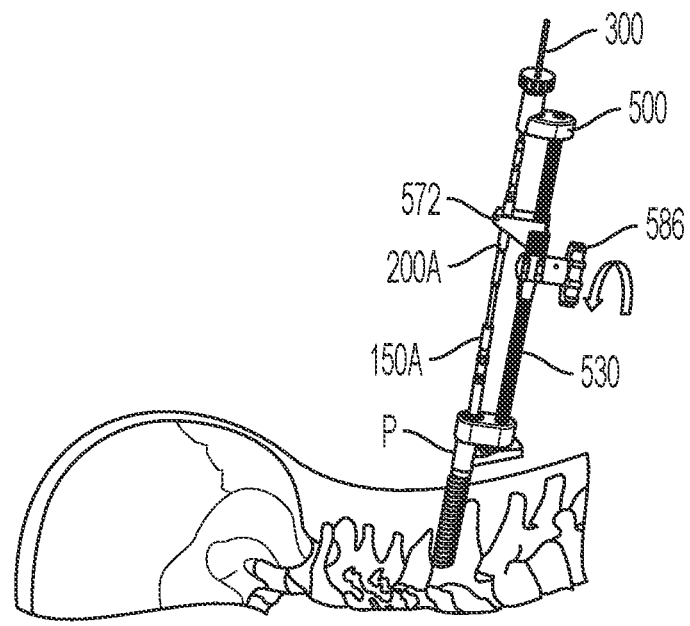
FIG. 52 is another truncated perspective view of the drill removal tool of FIG. 25, showing another step of the alternate technique.
Figure 53:
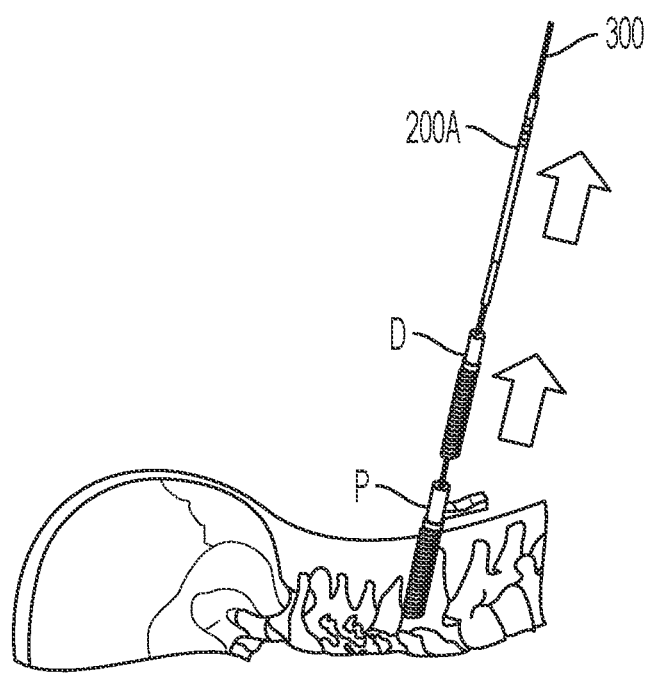
FIG. 53 is another truncated perspective view of the drill removal tool of FIG. 25, showing another step of the alternate technique.

K-wire 300 is advanced downwardly into drill bit 200A as shown in FIG. 50. Once long marking 303 is completely covered by drill bit 200A, knob 550 is rotated to the locked position as shown in FIG. 51. Wheel handle 586 is then rotated, as shown in FIG. 52, to move anvil 572 upwardly relative to toothed rack 530 and pull drill bit 200A out of the bone. Once drill bit 200A is pulled out of the bone, drill removal tool 500 and the drill bit can be lifted and removed. Drill tube 150A and dilator D can then be removed from protector P, as shown in FIG. 53.

Bone Screw Driver with K-Wire Retention

Referring to FIGS. 33-41, a bone screw driver 600 is shown according to one example. Bone screw driver 600 is designed to advance a bone screw over a K-wire and drive the bone screw into bone while preventing forward (i.e. distal) advancement of the K-wire. To accomplish this, bone screw driver 600 features a K-wire retention module 700. For purposes of this description, bone screw driver 600 and K-wire retention module 700 will be described in use with the same K-wire 300 described previously.

Bone screw driver 600 has a shaft 601 that defines a proximal end 602, a distal end 604 opposite the proximal end, and a longitudinal passage 606 between the proximal and distal ends. Passage 606 is configured such that bone screw driver 600 can be passed over the proximal end of K-wire 300 and advanced toward the distal end of the K-wire. Proximal end 602 has an attachment mechanism (not visible) over which a handle 603 is attached. The attachment mechanism can be any suitable structure for receiving a handle, including but not limited to a hex shaped shaft. Handle 603 is configured to be gripped by a user and rotated to operate the bone screw driver 600, much like a conventional screw driver. Distal end 604 has an external thread 605 configured to mate with an internal thread in a rod receiving component of a pedicle screw assembly. A knob 607 is provided on shaft 601 to facilitate rotation of the shaft to thread the external thread 605 into a rod receiving component.

Referring to FIGS. 34 and 35, distal end 604 has a driver tip 610. Driver tip 610 has a hexalobular extension 612 that fits into a similarly shaped recess in the head of the bone screw. Driver tip 610 also has a pair of tangs 614 located proximally relative to extension 612. Tangs 614 are configured to slide into diametrically opposed slots in a rod receiving component when external thread 605 is threaded into the internal thread of the rod receiver component. In this arrangement, tangs 614 occupy the location where a fixation rod will be located.

Figure 36:
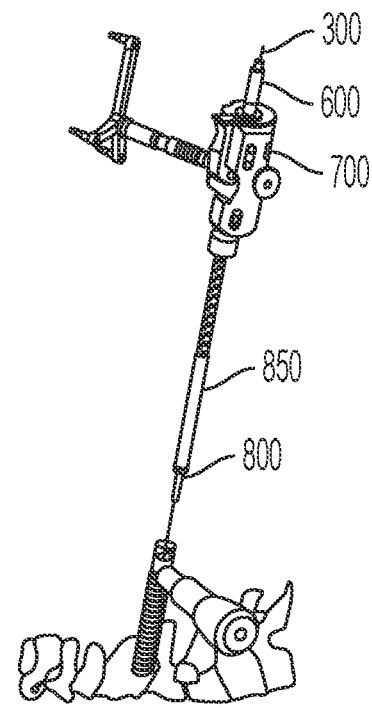
FIG. 36 is another perspective view of the bone screw driver with K-wire retention module of FIG. 33 during advancement over a K-wire.

K-wire retention module 700 includes a housing 710 having a proximal end 712, a distal end 714, and a passage 716 extending between the proximal and distal ends. Passage 716 aligns with passage 606 of bone screw driver 600. In this arrangement, bone screw driver 600 and K-wire retention module 700 can be advanced over K-wire 300 as a unit. FIG. 36 shows bone screw driver 600 (without handle 603 attached) in the process of being advanced over an implanted K-wire 300. Driver tip 610 is secured to a cannulated polyaxial screw assembly 800 and a tab protector sleeve 850 that also pass over K-wire 300.

Figure 37:
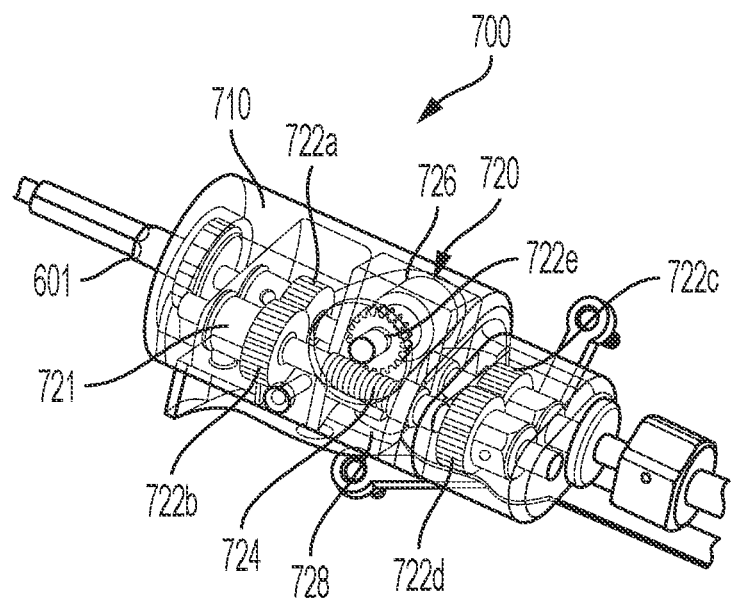
FIG. 37 is an enlarged truncated perspective view of the bone screw driver with K-wire retention module of FIG. 33, showing internal components of the K-wire retention module.

Referring to FIG. 37, K-wire retention module 700 has a roller assembly 720 contained within housing 710. Roller assembly 720 is operable in a disengaged mode and an engaged (or drive) mode. In the disengaged mode, roller assembly 720 allows K-wire retention module 700 and bone screw driver 600 to advance freely along the length of K-wire 300. In the engaged mode, roller assembly 720 engages K-wire 300 and feeds the K-wire through housing 710 in a proximal direction as bone screw driver 600 advances polyaxial screw assembly 800 in a distal direction.

Roller assembly 720 includes a first spur gear 722a attached to the shaft 601 of bone screw driver 600, and a second spur gear 722b mated with first spur gear 722a. Roller assembly 720 also includes third spur gear 722c on shaft 601 that is mated with a fourth spur gear 722d. Second spur gear 722b and fourth spur gear 722d are attached to a secondary shaft 721 that extends parallel to shaft 601. Secondary shaft 721 has a worm gear 724 mated with a fifth spur gear 722e. Fifth spur gear 722e is attached to a first roller 726, which is fixed to the fifth spur gear so that the fifth spur gear and first roller rotate in unison. A second roller 728 is positioned adjacent first roller 726 at a position to engage K-wire on a side opposite the first roller.

Figure 38:
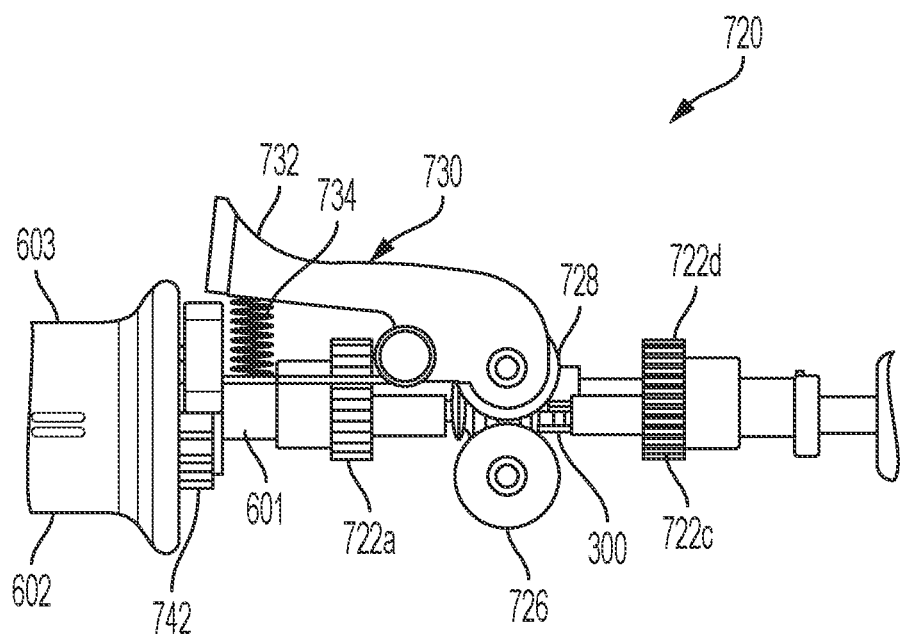
FIG. 38 is a side view of the K-wire retention module of FIG. 33, with some components removed for clarity, the K-wire retention module shown in a first mode of operation.
Figure 39:
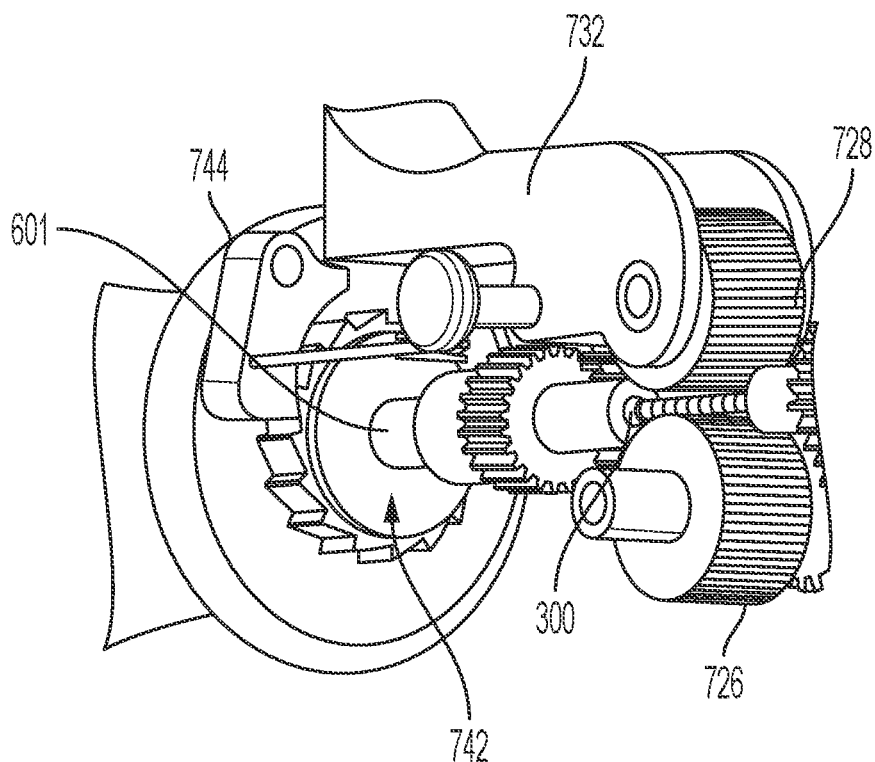
FIG. 39 is an enlarged truncated perspective view of the K-wire retention module components of FIG. 38 in the first mode of operation.
Figure 40:
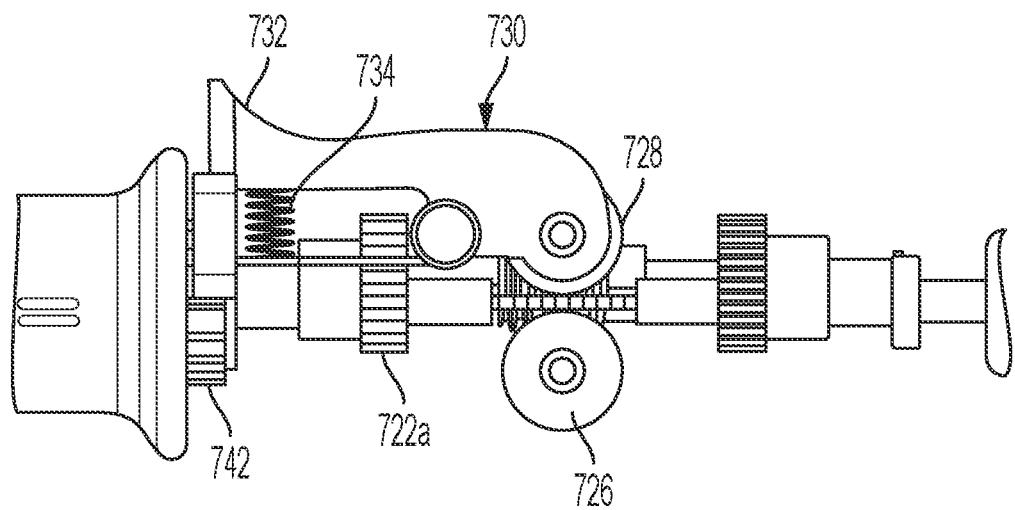
FIG. 40 is a side view of the K-wire retention module of FIG. 33, with some components removed for clarity, the K-wire retention module shown in a second mode of operation.

Referring to FIGS. 38-41, engagement and disengagement of roller assembly 720 is controlled by a lever assembly 730. Lever assembly 730 includes a spring-loaded lever 732 that is biased toward the engaged mode by a compression spring 734. FIG. 38 shows components of roller assembly 720 about to be advanced over K-wire 300. Lever 732 is positioned in the engaged mode by spring 734, which is fully expanded. In this mode, first and second rollers 726, 728 are positioned close together, with little or no clearance between them. To advance roller assembly 720 over K-wire 300, lever 732 is pressed inwardly toward the K-wire, as shown in FIG. 40. This moves first and second rollers 726, 728 apart, allowing the roller assembly 720 to advance over K-wire 300. Once K-wire 300 is received between first and second rollers 726, 728, lever 732 can be released to allow roller assembly 720 to return to the engaged mode under the bias of spring 734, which positions the rollers in direct engagement with the K-wire.

Polyaxial screw assembly 800 is driven into bone over K-wire 300 by applying clockwise torque to proximal end 602 of bone screw driver 600. When clockwise torque is applied to proximal end 602 of screw driver 600 with roller assembly 720 in the engaged mode, the roller assembly will feed K-wire 300 through housing 710 in the proximal direction. Clockwise rotation of shaft 601 rotates first spur gear 722a and third spur gear 722c in a clockwise direction, which in turn impart torque to secondary shaft 721 through second spur gear 722c and fourth spur gear 722d. Secondary shaft 721 and worm gear 724 rotate in a counterclockwise direction, which imparts torque to fifth spur gear 722e. Fifth spur gear 722e drives first roller 726 in a first direction. Second roller 728 is biased into engagement with K-wire 300 and rotates in a second direction opposite first direction. The outer surfaces of first and second rollers 726, 728 grip the surface of K-wire 300 to draw the K-wire in the proximal direction relative to housing 710, so that the K-wire is fed proximally as polyaxial screw assembly 800 is driven distally into bone.

Figure 41:
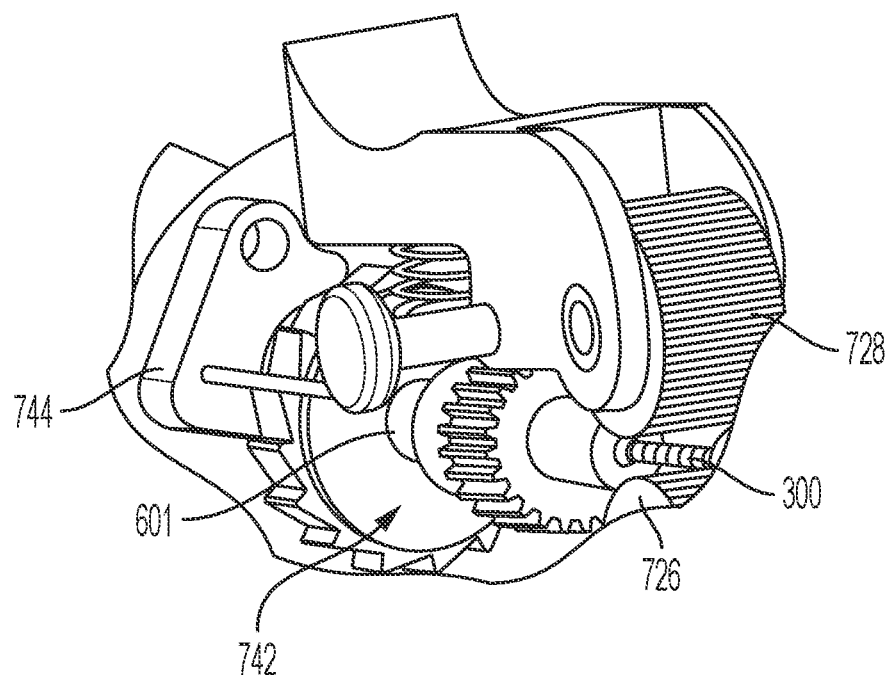
FIG. 41 is an enlarged truncated perspective view of the K-wire retention module components of FIG. 40 in the second mode of operation.
Figure 42:
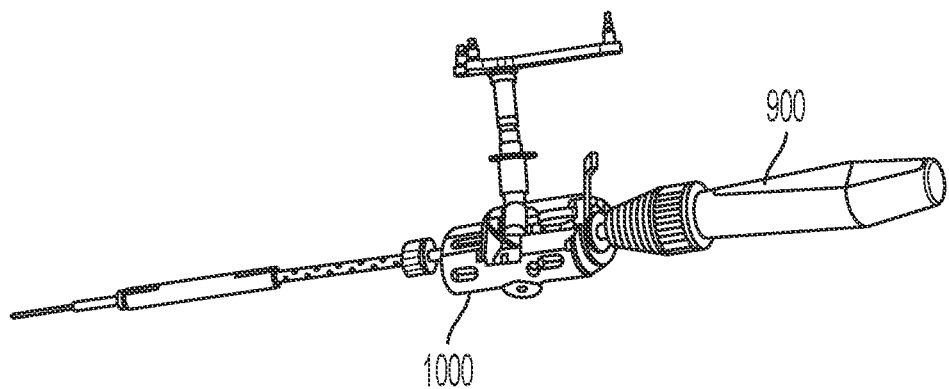
FIG. 42 is a perspective view of an alternate bone screw driver with K-wire retention module according to another aspect of the present disclosure, with the bone screw driver and K-wire retention module passed over a K-wire.

Distal feeding of K-wire 300 through housing 710 is prevented by a ratchet wheel 742 and pawl 744. Pawl 744 engages ratchet wheel 742, as shown in FIG. 39, to prevent shaft 601 from being rotated counterclockwise relative to housing 710, which would rotate first and second rollers 726, 728 in a reverse direction that feeds K-wire distally. Pawl 744 can be pivoted out of engagement with ratchet wheel 742 by pressing lever 732 inwardly against spring 724, as shown in FIG. 41. This switches the roller assembly 720 to the disengaged mode and releases K-wire 300, allowing bone screw driver 600 and K-wire retention module 700 to be removed from K-wire without risk of distally advancing the K-wire.

K-wire retention modules according to the present disclosure can be modular units that are detachably connectable to different types of instruments, including but not limited to instruments for tapping and driving. In the present example, K-wire retention module 700 is detachably connected to bone screw driver 600 with a quick fit connection 650 represented in FIG. 33. Shaft 601 of bone screw driver 600 snaps into housing 710 using quick fit connection 650, which can be a hex drive, ¼ inch drive or AO drive that controls rotation.

Bone screw drivers according to the present disclosure can include various types of indicia for aiding the insertion of a bone screw. For example, shaft 601 can have spaced lines that provide depth markings, similar to those on universal drill guide 110. Depth markings can provide the user with a visual indication of the depth to which the tip of the bone screw is advanced. Bone screw drivers can also include various features to aid in sterilization. For example, shaft 601 has a series of apertures 611 that allows steam to access the inside of the shaft during autoclaving and cleaning.

Figure 43:
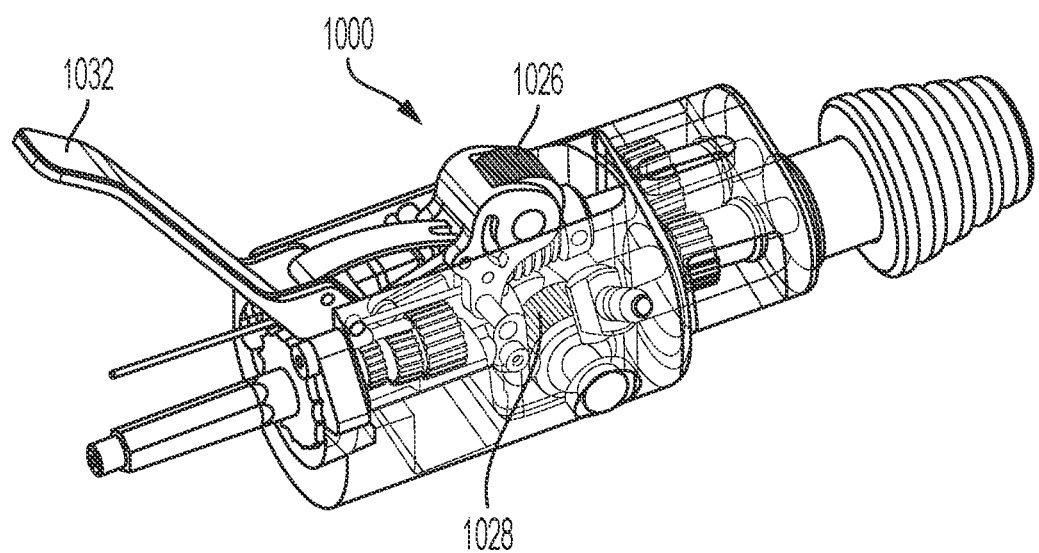
FIG. 43 is a perspective view of the bone screw driver with K-wire retention module of FIG. 42, showing internal components of the K-wire retention module in a first mode of operation.
Figure 44:
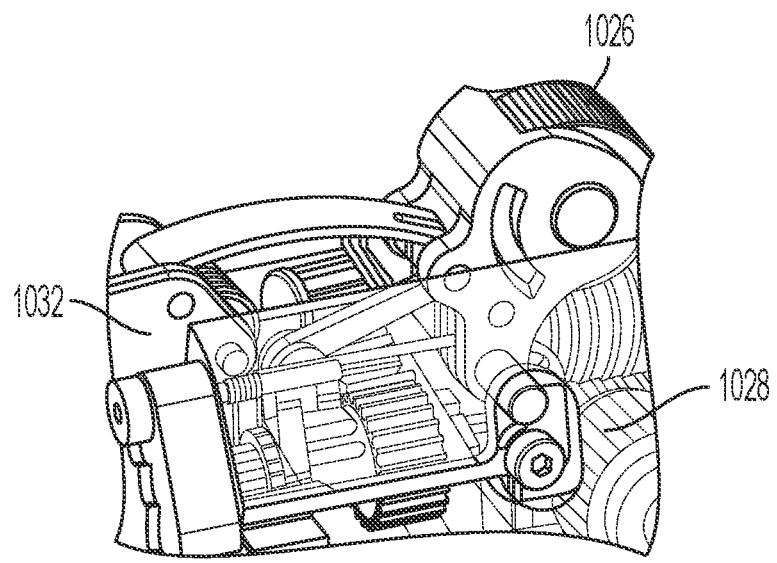
FIG. 44 is an enlarged perspective view of the internal components of the K-wire retention module of FIG. 43 in the first mode of operation.
Figure 45:
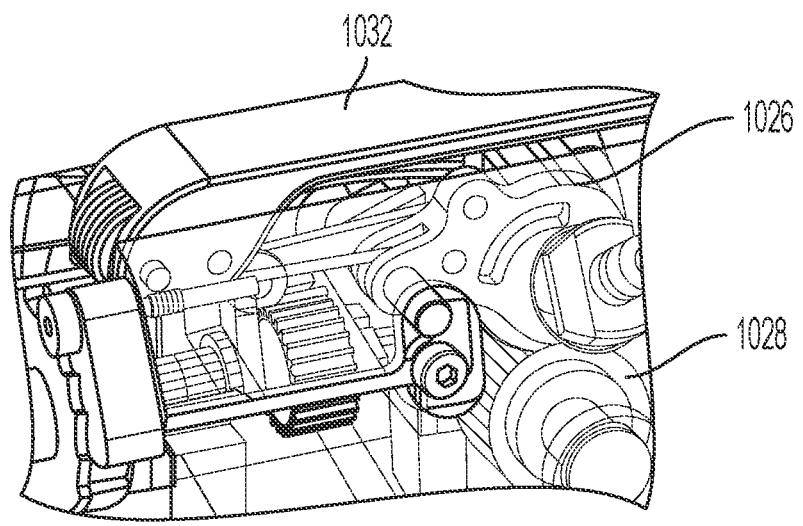
FIG. 45 is an enlarged perspective view of the internal components of the K-wire retention module of FIG. 43 in a second mode of operation.
Figure 46:
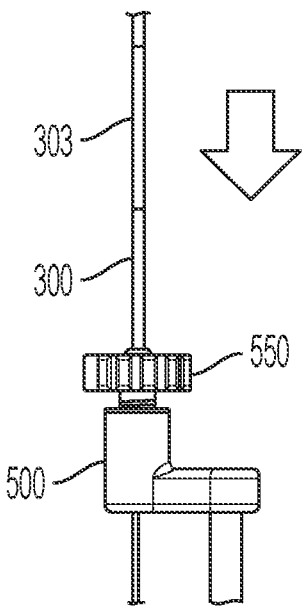
FIG. 46 is an enlarged truncated perspective view of the drill removal tool of FIG. 25, showing one step of an alternate technique for using the drill removal tool.
Figure 47:
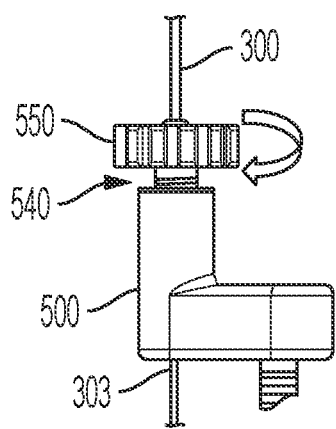
FIG. 47 is another enlarged truncated perspective view of the drill removal tool of FIG. 25, showing another step of the alternate technique.

FIGS. 42-45 show an alternate bone screw driver 900 and K-wire retention module 1000 according to another embodiment. K-wire retention module 1000 is similar to K-wire retention module 700, but features a pinch lever 1032 and pinch rollers 1026, 1028. Pinch lever 1032 is normally in an open position to separate pinch rollers 1026, 1028, as shown in FIGS. 43 and 44. Pinch lever 1032 can be moved to a closed position, as shown in FIG. 45, to engage the rollers against K-wire 300. Pinch lever 1032 can only stay closed (i.e. the drive can only remain engaged) when K-wire 300 is positioned between pinch rollers 1026, 1028.

The instruments described herein can be manufactured using various materials, including but not limited to various alloys of stainless steel. Alloy grade can be selected based on desired strength, hardness, corrosion resistance, galling properties and other performance criteria.

Accordingly, it is intended that the appended claims cover all such variations as fall within the scope of the present disclosure.

What is claimed is:

1. A universal drill guide for guiding a surgical drill bit during a procedure, the universal drill guide having a guide body comprising:

a proximal end defining a proximal opening adapted to receive a drill bit through the guide body;
a distal end defining a distal opening configured to connect to a drill tube and to receive a drill bit received through the proximal opening; and
a drill stop extending from the proximal end in a direction opposite from the distal end along a longitudinal axis of the guide body and configured to limit a depth of insertion of a drill bit through the proximal end of the guide body;
wherein the drill stop comprises a shaft extending from the proximal end of the guide body and a stop member extending laterally from the shaft;
wherein the stop member defines a slot adapted to receive a drill bit, the stop member alignable with the proximal opening and configured to limit passage of the drill bit through the slot so as to limit the depth of insertion of the drill bit through the proximal opening; and
wherein the shaft is axially movable relative to the guide body to raise and lower the drill stop and set a desired depth for drilling.

2. A universal drill guide system comprising:
(A) a plurality of interchangeable drill bits, each drill bit having a different outer diameter for drilling a different size hole;
(B) a plurality of interchangeable drill tubes, each drill tube defining a bore having a different inner diameter; and
(C) a universal drill guide having a guide body, the guide body comprising:
a proximal end defining a proximal opening adapted to receive one of the drill bits into the guide body;
a distal end defining a distal opening configured to detachably connect to one of the drill tubes and to receive said one of the drill bits; and
a drill stop extending from the proximal end of the guide body in a direction opposite from the distal end along a longitudinal axis of the guide body, the drill stop configured to limit a depth of insertion of said one of the drill bits into the guide body,
the proximal and distal openings being axially aligned to permit advancement of said one of the drill bits through the guide body and through said one of the drill tubes to a drilling location.

3. The universal drill guide system of claim 2, wherein the plurality of interchangeable drill bits comprises a first drill bit and a second drill bit having a larger outer diameter than the first drill bit, and the plurality of interchangeable drill tubes comprises a first drill tube and a second drill tube having a larger inner diameter than the first drill tube.

4. The universal drill guide system of claim 3, wherein the first drill tube is configured to guide advancement of the first drill bit and keep the first drill bit axially stable during drilling, and the second drill tube is configured to guide advancement of the second drill bit and keep the second drill bit axially stable during drilling.

5. The universal drill guide system of claim 4, wherein the first drill bit and first drill tube comprise identical first indicia, and the second drill bit and second drill tube comprise identical second indicia, the identical second indicia being different from the identical first indicia.

6. The universal drill guide system of claim 3, wherein the first and second drill bits are each cannulated and configured to retain a guide element.

7. The universal drill guide system of claim 2, wherein each drill bit comprises a reduced diameter section and an enlarged diameter section adjacent to the reduced diameter section, forming a stop surface configured to abut the drill stop to limit advancement of said drill bit through the guide body.

\* \* \* \* \*